111 US005891673A

United States Patent [19]
Hashimoto et al.

[11] Patent Number: 5,891,673
[45] Date of Patent: Apr. 6, 1999

[54] LCK BINDING PROTEIN

[75] Inventors: Yasuhiro Hashimoto; Yoshihiro Takemoto, both of Tsukuba, Japan

[73] Assignee: Syntex (U.S.A.) Inc., Palo Alto, Calif.

[21] Appl. No.: 942,423

[22] Filed: Oct. 1, 1997

Related U.S. Application Data

[63] Continuation of Ser. No. 362,715, Dec. 23, 1994, abandoned.

[51] Int. Cl.[6] .................................................. C12N 15/00
[52] U.S. Cl. ........................ 435/69.1; 530/350; 530/300; 435/7.1; 435/194
[58] Field of Search ..................................... 530/300, 350; 435/7.1, 69.1, 194

[56] References Cited

PUBLICATIONS

Ngo et al. (1994) In; The protein Folding Problem and Tertiory Structure Production. Merz et al (eds) Birkhauser: Boston pp. 433,493–495.
Kitemura et al. 1995 Biochem. Biophys Res. Comm. 208: 1137–1146.
Yoshihiro Takemoto et al. 1995 EMBO J. 14: 3403–3414.

*Primary Examiner*—Lila Feisee
*Assistant Examiner*—Eliane Lazar-Wesley
*Attorney, Agent, or Firm*—Heller Ehrman White & McAuliffe

[57] ABSTRACT

Murine Lck binding protein ("LckBP1"), cDNA encoding for LckBP1, and protein and cDNA fragments and analogs, are cloned and expressed and characterized.

5 Claims, 8 Drawing Sheets

Fig. 1A

```
-59                                          CAGCCGCTGGAGGGGGCGCCTGGTGTAGATGTGAAAAGCCGTAACCAGAACCAGTAAAG
  1  ATGTGGAAGTCTGTAGTGGGACATGATGTATCGGTTCCGTTGGAGACCCAGGTGATGACTGGGATACAGACCCTGACTTTGTGAATGAC
      M  W  K  S  V  V  G  H  D  V  S  V  E  T  Q  G  D  D  W  D  T  D  P  D  F  V  N  D

91  ATCTCCGAGAAGGAGCAACGGTGGGAGCCAAGACCATTGAGGGCTCTGGACGCCACAGAGCACATCAACATCCACCAGCTGAGGAACAAA
      I  S  E  K  E  Q  R  W  G  A  K  T  I  E  G  S  G  R  T  E  H  I  N  I  H  Q  L  R  N  K

181  GTGTCAGAGGAGCACGACATCCTCAAGAAGAAGGAGCTGGAATCGGGCCCTAAGGCATCCATGGCTATGCGGTCAGTTTGGAGTGGAG
      V  S  E  E  H  D  I  L  K  K  K  E  L  E  S  G  P  K  A  S  H  G  Y  G  G  Q  F  G  V  E

271  AGAGACCGGATGGACAAGAGTGCCGTGGGCCACGAGTATGTTGCTGATGTGGAGAAACACTCATCTCAGACTGATGCCGCCAGAGGCTTT
      R  D  R  M  D  K  S  A  V  G  H  E  Y  V  A  D  V  E  K  H  S  S  Q  T  D  A  A  R  G  F

361  GGGGGCAAATATGGAGTTGAGAGGGACAGGGACAAGAGTGCTTTGACTACAAAGGAGAAGTGGAAAAGCATGCATCTCAG
      G  G  K  Y  G  V  E  R  D  R  A  D  K  S  A  V  G  F  D  Y  K  G  E  V  E  K  H  A  S  Q

451  AAAGATTACTCTCATGGCTTTGGTGGCGGCTACCGGGTAGAGAAGGATAAACGGGACAAAGCAGCCCTGGGATACGACTACAAAGGAGAG
      K  D  Y  S  H  G  F  G  G  R  Y  G  V  E  K  D  K  R  D  K  A  A  L  G  Y  D  Y  K  G  E

541  ACGGAGAAGCACGAGTCTCAGAGAGATTATGCCAAGGGCTTTGGTGGCCAATATGGAATCCAGAAAGACCGAGTTGATAAGAGTGCTGTT
      T  E  K  H  E  S  Q  R  D  Y  A  K  G  F  G  G  Q  Y  G  I  Q  K  D  R  V  D  K  S  A  V

631  GGCTTCAATGAAATGGAGGCCCCAACCACGGCTATAAGAAGACAACACCCATAGAAGCTGCTTCCAGTGGTGCCCGTGGGCTGAAGGCA
      G  F  N  E  M  E  A  P  T  T  A  Y  K  K  T  T  P  I  E  A  A  S  S  G  A  R  G  L  K  A

721  AAATTTGAGTCCCTGGCTGAGGAAGAGAAGCGCAAGAGGGAAGAGGAAAAGGCACAGCAGATGGCCAGGCAGCAACAGGAGCGAAGGCT
      K  F  E  S  L  A  E  E  K  R  K  R  E  E  E  E  K  A  Q  Q  M  A  R  Q  Q  E  R  K  A
```

Fig. 1B

```
                                                                                                 37 a.a.
                                                                                                 tandem
                                                                                                 repeat LBP1      1   MWKSVVGHDV  SVSVETQG.D  DWDTDPDFVN  DISEKEQRWG  AKTIEGSGRT
HS1       1   ----------  ----------  ----------  ----------  ----------
P80/85    1   ---ASA---A-  -ITQDDG-A-  ---E------  ---V------  ---VQ---HQ LBP1     50   EHINIHQLRN  KVSEEHDILK  KKELESGPKA  SHGYGGQFGV  ERDRMDKSAV
HS1      50   ----------  ------V-R-  ---M------  ------R---  ----------
P80/85   51   ------K--E  N-FQ--QT--  K----T----  ------K---  ---Q-----R---

LBP1    100   GHEYVADVEK  HSSQTDAARG  FGGKYGVERD  RADKSAVGFD  YKGEVEKHAS
HS1     100   ------E---  ------K---  ----------  ------K---  -------T--
P80/85  101   ----QSKLS-  -C---V-SV-  ---F---QM-  --V-Q-----E  --Q-KT----

LBP1    150   QKDYSHGFGG  RYGVEKDKRD  KAALGYDYKG  ETEKHESQRD  YAKGFGGQYG
HS1     150   ------R---  ----W-----  ----------  ----------  ----------
P80/85  151   ------S---  ----QA-RV-  -S-V-F--Q-  K-------K-  --S------K-

LBP1    200   IQKDRVDKSA  VG........  ..........  ..........  ..........
HS1     200   ----------  ..........  ..........  ..........  ..........
P80/85  201   -D--K-----  --FEYQGKTE  KHESQKDYVK  GFGGKFGVQT  DRQDKCALGW

LBP1          ..........  ..........  ..........  ..........  ..........
HS1           ..........  ..........  ..........  ..........  ..........
P80/85  251   DHQEKLQLHE  SQKDYKTGFG  GKFGVQSERQ  DSSAVGFDYK  ERLAKHEPQQ

LBP1    212   ..........  ...FNEMEAP  TTAYKKTTPI  EAASSGARGL
HS1     212   ..........  ----------  ----------  ----------
P80/85  301   DYAKGFGGKY  GVQKDRMDKN  AST-E-VVQV  PS--Q--V--  --VT-KTSNI
```

Fig. 2A

```
LBP1   239  KAKFESLAEE  K....RKREE  EEKAQQMARQ  QQERKAVVKM  SREVQQPSMP
HS1    239  -------M--  ----------  -----V--R-  -----T-R--  ---AP--VIA
P80/85 351  R-N--N--K-  REQED-RKA-  A-R--R--KE  R--QEEA...  ..........      Pro rich
                                                                           &
LBP1   285  VEEPAAPAQL  PKKISSEVWP  PAESHLPPES  QPVRSRREYP  VPSLPTRQSP      E1A
HS1    285  M-----V-P-  -------A--  --VGTPPSS--  E---TS--H-  ---L--I--T.
P80/85 388  ..........  RR-LEEQARA  KKQT...-A-  .-SPQPI-DR  P--S-IYEDA LBP1   335  LQNHLEDNEE  PPALPPRTPE  GLQVVEEPVY  EAAPELEPEP  EPDYEPEPET
HS1    334  ----------  ...LP-----  -------L--  ----I-----  --EP----P-
P80/85 425  APF....KA-  -SYRGS....  ....EP--E-  SIEAAGI--A  GSQQGLTYTS LBP1   385  EPDYEDVGEL  DR..QDEDAE  GDYEDVLEPE  D......TP  SLSYQAGPSA
HS1    375  -N-----E-M  --HE-EDEP-  -----E----  ----------  -SGCP--AG-
P80/85 463  --V--TTEAP  GHYQAED-TY  DG---SD-..  -SSFSSALAG  ..........

LBP1   426  GAGGAGISAI  ALYDYQGEGS  DELSFDPDDI  ITDIEMVDEG  WWRGQCRGHF      SH3
HS1    425  --VAL----V  ----------  ---------V  ----------  ----R-H---
P80/85 490  ......--T-  ----AA-D--  ----I-----  --N----I-D-  ---V-K-RY

LBP1   476  GLFPANYVKL  L
HS1    475  ----------  -E
P80/85 535  ------E---  RQ
```

Fig. 2B

P1 274 MSREVQQPSMPVEEPAAPAQLPKKISSE 301
P2 302 VWPPAESHLPPESQPVRSRREYPVPSLPTRQSPL 335
P3 336 QNHLEDNEEPPALPPRTPEGLQVVE 360
P4 354 EGLQVVEEPVYEAAPELEPEPEPDYEPEPETEPDYE 390

SEQUENCE LISTING ( 1 ) GENERAL INFORMATION:

( i i i ) NUMBER OF SEQUENCES: 68

( 2 ) INFORMATION FOR SEQ ID NO:1:

( i ) SEQUENCE CHARACTERISTICS:
        ( A ) LENGTH: 2003 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: murine ( v i i ) IMMEDIATE SOURCE:
        ( B ) CLONE: LBP1

( x i ) SEQUENCE DESCRIPTION: SEQ ID NO:1:

```
CAGCCGCTGG  AGGGGGCGCC  TGGTGTAGAT  GTGAAAAGCC  GTAACCAGGA  ACCAGTAAAG      60

ATGTGGAAGT  CTGTAGTGGG  GCATGATGTA  TCGGTTTCCG  TGGAGACCCA  GGGTGATGAC     120

TGGGATACAG  ACCCTGACTT  TGTGAATGAC  ATCTCCGAGA  AGGAGCAACG  GTGGGGAGCC     180

AAGACCATTG  AGGGCTCTGG  ACGCACAGAG  CACATCAACA  TCCACCAGCT  GAGGAACAAA     240
```

-continued

| | | | | | |
|---|---|---|---|---|---|
|GTGTCAGAGG|AGCACGACAT|CCTCAAGAAG|AAGGAGCTGG|AATCGGGGCC|TAAGGCATCC 300|
|CATGGCTATG|GCGGTCAGTT|TGGAGTGGAG|AGAGACCGGA|TGGACAAGAG|TGCCGTGGGC 360|
|CACGAGTATG|TTGCTGATGT|GGAGAAACAC|TCATCTCAGA|CTGATGCCGC|CAGAGGCTTT 420|
|GGGGGCAAAT|ATGGAGTTGA|GAGGGACCGG|GCAGACAAGT|CAGCGGTGGG|CTTTGACTAC 480|
|AAAGGAGAAG|TGGAAAAGCA|TGCATCTCAG|AAAGATTACT|CTCATGGCTT|TGGTGGCCGC 540|
|TACGGGGTAG|AGAAGGATAA|ACGGACAAA|GCAGCCCTGG|GATACGACTA|CAAAGGAGAG 600|
|ACGGAGAAGC|ACGAGTCTCA|GAGAGATTAT|GCCAAGGGCT|TTGGTGGCCA|ATATGGAATC 660|
|CAGAAAGACC|GAGTGGATAA|GAGTGCTGTT|GGCTTCAATG|AAATGGAGGC|CCCAACCACG 720|
|GCGTATAAGA|AGACAACACC|CATAGAAGCT|GCTTCCAGTG|GTGCCCGTGG|GCTGAAGGCA 780|
|AAATTTGAGT|CCCTGGCTGA|GGAGAAGAGG|AAGCGAGAGG|AAGAAGAGAA|GGCACAGCAG 840|
|ATGGCCAGGC|AGCAACAGGA|GCGAAAGGCT|GTGGTAAAGA|TGAGCCGAGA|AGTCCAGCAG 900|
|CCATCCATGC|CTGTGGAAGA|GCCAGCGGCA|CCAGCCCAGT|TGCCCAAGAA|GATCTCCTCA 960|
|GAGGTCTGGC|CTCCAGCAGA|GAGTCACCTA|CCGCCAGAGT|CTCAGCCAGT|GAGAAGCAGA 1020|
|AGGGAATACC|CTGTGCCCTC|TCTGCCCACG|AGGCAGTCTC|CATTGCAGAA|TCACTTGGAG 1080|
|GACAACGAGG|AGCCCCCAGC|TCTGCCCCCT|AGGACCCCAG|AAGGCCTCCA|GGTGGTGGAA 1140|
|GAGCCAGTGT|ACGAAGCAGC|ACCCGAGCTG|GAGCCGGAGC|CAGAGCCTGA|CTATGAGCCA 1200|
|GAGCCAGAGA|CAGAGCCTGA|CTATGAGGAT|GTTGGGGAGT|TAGATCGGCA|GGATGAGGAT 1260|
|GCAGAGGGAG|ACTATGAGGA|TGTGCTGGAG|CCCGAGGACA|CCCCTTCTCT|GTCCTACCAA 1320|
|GCTGGACCCT|CAGCTGGGGC|TGGTGGTGCG|GGGATCTCTG|CTATAGCCCT|GTATGATTAC 1380|
|CAAGGAGAGG|GAAGCGATGA|GCTTTCCTTT|GATCCAGATG|ACATCATCAC|TGACATTGAG 1440|
|ATGGTGGATG|AAGGCTGGTG|GCGGGGCCAA|TGCCGTGGCC|ACTTTGGACT|TTTCCCTGCA 1500|
|AACTATGTCA|AGCTCCTCTA|ATGACCAGCC|CATTGTCTTC|CGACTTCCCG|AATTCGAAGC 1560|
|TGCTCTGCCT|CCCTCTTCCC|ACTCCATGGT|ACTGCTGCAA|GGACCTGGCT|GAACATCATG 1620|
|AGATGCCTGA|AGTTCTGGCA|GTCTGTCTCC|CGCCTCTTTA|AGAGCTTTAG|GTAGAATCGC 1680|
|TCCAGGTGGG|GGTGGGGGTG|GGGGTGGGAT|CCCTCTGTCC|CTCTGTGACC|ACTCTTCCCT 1740|
|GAGGTAGCTC|ATGAAATCAT|CTTGCAGACC|TGCCTCCTTC|AGCCGCACCC|CAGCTCTGCC 1800|
|AACCTTGCTC|TAGAGTGCTG|GGATTCCCTT|GCCCCGACCC|TGGGTGCCAG|CCTAGAGGGG 1860|
|AGGCTCTCAC|AGGGCTGCCT|GATTCGCCCT|GTTGTGCTTT|TGCTCATTTT|TCTTCCCTTA 1920|
|GCAGACAAAT|TGGAACTGCC|CTTCTGTTTA|GTCCTAAAAC|TGAAAATAAA|ATGAGACTGT 1980|
|GGCTAAAAAA|AAAAAAAAAA|AAA| | | 2003|

( 2 ) INFORMATION FOR SEQ ID NO:2:

( i ) SEQUENCE CHARACTERISTICS:
        ( A ) LENGTH: 486 amino acids
        ( B ) TYPE: amino acid
        ( C ) STRANDEDNESS: Not Relevant
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: HS1

( x i ) SEQUENCE DESCRIPTION: SEQ ID NO:2:

| Met | Trp | Lys | Ser | Val | Val | Gly | His | Asp | Val | Ser | Val | Ser | Val | Glu | Thr |
|---|---|---|---|---|---|---|---|---|---|---|---|---|---|---|---|
| 1 | | | | 5 | | | | | 10 | | | | | 15 | |
| Gln | Gly | Asp | Asp | Trp | Asp | Thr | Asp | Pro | Asp | Phe | Val | Asn | Asp | Ile | Ser |
| | | | 20 | | | | 25 | | | | | | 30 | | |
| Glu | Lys | Glu | Gln | Arg | Trp | Gly | Ala | Lys | Thr | Ile | Glu | Gly | Ser | Gly | Arg |
| | | 35 | | | | | 40 | | | | | 45 | | | |
| Thr | Glu | His | Ile | Asn | Ile | His | Gln | Leu | Arg | Asn | Lys | Val | Ser | Glu | Glu |
| | 50 | | | | | 55 | | | | | 60 | | | | |
| His | Asp | Ile | Leu | Lys | Lys | Lys | Glu | Leu | Glu | Ser | Gly | Pro | Lys | Ala | Ser |
| 65 | | | | | 70 | | | | | 75 | | | | | 80 |
| His | Gly | Tyr | Gly | Gly | Gln | Phe | Gly | Val | Glu | Arg | Asp | Arg | Met | Asp | Lys |
| | | | | 85 | | | | | 90 | | | | | 95 | |
| Ser | Ala | Val | Gly | His | Glu | Tyr | Val | Ala | Asp | Val | Glu | Lys | His | Ser | Ser |
| | | | 100 | | | | | 105 | | | | | 110 | | |
| Gln | Thr | Asp | Ala | Ala | Arg | Gly | Phe | Gly | Gly | Lys | Tyr | Gly | Val | Glu | Arg |
| | | 115 | | | | | 120 | | | | | 125 | | | |
| Asp | Arg | Ala | Asp | Lys | Ser | Ala | Val | Gly | Phe | Asp | Tyr | Lys | Gly | Glu | Val |
| | 130 | | | | | 135 | | | | | 140 | | | | |
| Glu | Lys | His | Ala | Ser | Gln | Lys | Asp | Tyr | Ser | His | Gly | Phe | Gly | Gly | Arg |
| 145 | | | | | 150 | | | | | 155 | | | | | 160 |
| Tyr | Gly | Val | Glu | Lys | Asp | Lys | Arg | Asp | Lys | Ala | Ala | Leu | Gly | Tyr | Asp |
| | | | | 165 | | | | | 170 | | | | | 175 | |
| Tyr | Lys | Gly | Glu | Thr | Glu | Lys | His | Glu | Ser | Gln | Arg | Asp | Tyr | Ala | Lys |
| | | | 180 | | | | | 185 | | | | | 190 | | |
| Gly | Phe | Gly | Gly | Gln | Tyr | Gly | Ile | Gln | Lys | Asp | Arg | Val | Asp | Lys | Ser |
| | | 195 | | | | | 200 | | | | | 205 | | | |
| Ala | Val | Gly | Phe | Asn | Glu | Met | Glu | Ala | Pro | Thr | Thr | Ala | Tyr | Lys | Lys |
| | 210 | | | | | 215 | | | | | 220 | | | | |
| Thr | Thr | Pro | Ile | Glu | Ala | Ala | Ser | Ser | Gly | Ala | Arg | Gly | Leu | Lys | Ala |
| 225 | | | | | 230 | | | | | 235 | | | | | 240 |
| Lys | Phe | Glu | Ser | Leu | Ala | Glu | Glu | Lys | Arg | Lys | Arg | Glu | Glu | Glu | Glu |
| | | | | 245 | | | | | 250 | | | | | 255 | |
| Lys | Ala | Gln | Gln | Met | Ala | Arg | Gln | Gln | Glu | Arg | Lys | Ala | Val | Val |
| | | | 260 | | | | | 265 | | | | | 270 | | |
| Lys | Met | Ser | Arg | Glu | Val | Gln | Gln | Pro | Ser | Met | Pro | Val | Glu | Glu | Pro |
| | | 275 | | | | | 280 | | | | | 285 | | | |
| Ala | Ala | Pro | Ala | Gln | Leu | Pro | Lys | Lys | Ile | Ser | Ser | Glu | Val | Trp | Pro |
| | 290 | | | | | 295 | | | | | 300 | | | | |
| Pro | Ala | Glu | Ser | His | Leu | Pro | Pro | Glu | Ser | Gln | Pro | Val | Arg | Ser | Arg |
| 305 | | | | | 310 | | | | | 315 | | | | | 320 |
| Arg | Glu | Tyr | Pro | Val | Pro | Ser | Leu | Pro | Thr | Arg | Gln | Ser | Pro | Leu | Gln |
| | | | | 325 | | | | | 330 | | | | | 335 | |
| Asn | His | Leu | Glu | Asp | Asn | Glu | Glu | Pro | Ala | Leu | Pro | Pro | Arg | Thr |
| | | | 340 | | | | | 345 | | | | | 350 | | |
| Pro | Glu | Gly | Leu | Gln | Val | Val | Glu | Glu | Pro | Val | Tyr | Glu | Ala | Ala | Pro |
| | | 355 | | | | | 360 | | | | | 365 | | | |
| Glu | Leu | Glu | Pro | Glu | Pro | Glu | Pro | Asp | Tyr | Glu | Pro | Glu | Pro | Glu | Thr |
| | 370 | | | | | 375 | | | | | 380 | | | | |
| Glu | Pro | Asp | Tyr | Glu | Asp | Val | Gly | Glu | Leu | Asp | Arg | Gln | Asp | Glu | Asp |
| 385 | | | | | 390 | | | | | 395 | | | | | 400 |
| Ala | Glu | Gly | Asp | Tyr | Glu | Asp | Val | Leu | Glu | Pro | Glu | Asp | Thr | Pro | Ser |
| | | | | 405 | | | | | 410 | | | | | 415 | |

| Leu | Ser | Tyr | Gln<br>420 | Ala | Gly | Pro | Ser | Ala<br>425 | Gly | Ala | Gly | Gly | Ala<br>430 | Gly | Ile |
|---|---|---|---|---|---|---|---|---|---|---|---|---|---|---|---|
| Ser | Ala | Ile | Ala<br>435 | Leu | Tyr | Asp | Tyr<br>440 | Gln | Gly | Glu | Gly | Ser<br>445 | Asp | Glu | Leu |
| Ser | Phe<br>450 | Asp | Pro | Asp | Asp | Ile<br>455 | Ile | Thr | Asp | Ile | Glu<br>460 | Met | Val | Asp | Glu |
| Gly<br>465 | Trp | Trp | Arg | Gly | Gln<br>470 | Cys | Arg | Gly | His | Phe<br>475 | Gly | Leu | Phe | Pro | Ala<br>480 |
| Asn | Tyr | Val | Lys | Leu<br>485 | Leu | | | | | | | | | | |

(2) INFORMATION FOR SEQ ID NO:3:

(i) SEQUENCE CHARACTERISTICS:
        (A) LENGTH: 486 amino acids
        (B) TYPE: amino acid
        (C) STRANDEDNESS: Not Relevant
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: LCK BINDING PROTEIN (xi) SEQUENCE DESCRIPTION: SEQ ID NO:3:

| Met<br>1 | Trp | Lys | Ser | Val<br>5 | Val | Gly | His | Asp | Val<br>10 | Ser | Val | Ser | Val<br>15 | Glu | Thr |
|---|---|---|---|---|---|---|---|---|---|---|---|---|---|---|---|
| Gln | Gly | Asp | Asp<br>20 | Trp | Asp | Thr | Asp | Pro<br>25 | Asp | Phe | Val | Asn | Asp<br>30 | Ile | Ser |
| Glu | Lys | Glu<br>35 | Gln | Arg | Trp | Gly | Ala<br>40 | Lys | Thr | Ile | Glu | Gly<br>45 | Ser | Gly | Arg |
| Thr | Glu<br>50 | His | Ile | Asn | Ile | His<br>55 | Gln | Leu | Arg | Asn | Lys<br>60 | Val | Ser | Glu | Glu |
| His<br>65 | Asp | Val | Leu | Arg | Lys<br>70 | Lys | Glu | Met | Glu | Ser<br>75 | Gly | Pro | Lys | Ala | Ser<br>80 |
| His | Gly | Tyr | Gly | Gly<br>85 | Arg | Phe | Gly | Val | Glu<br>90 | Arg | Asp | Arg | Met | Asp<br>95 | Lys |
| Ser | Ala | Val | Gly<br>100 | His | Glu | Tyr | Val | Ala<br>105 | Glu | Val | Glu | Lys | His<br>110 | Ser | Ser |
| Gln | Thr | Asp<br>115 | Ala | Ala | Lys | Gly | Phe<br>120 | Gly | Gly | Lys | Tyr | Gly<br>125 | Val | Glu | Arg |
| Asp | Arg<br>130 | Ala | Asp | Lys | Ser | Ala<br>135 | Val | Gly | Phe | Asp | Tyr<br>140 | Lys | Gly | Glu | Val |
| Glu<br>145 | Lys | His | Thr | Ser | Gln<br>150 | Lys | Asp | Tyr | Ser | Arg<br>155 | Gly | Phe | Gly | Gly | Arg<br>160 |
| Tyr | Gly | Val | Glu | Lys<br>165 | Asp | Lys | Trp | Asp | Lys<br>170 | Ala | Ala | Leu | Gly | Tyr<br>175 | Asp |
| Tyr | Lys | Gly | Glu<br>180 | Thr | Glu | Lys | His | Glu<br>185 | Ser | Gln | Arg | Asp | Tyr<br>190 | Ala | Lys |
| Gly | Phe | Gly<br>195 | Gly | Gln | Tyr | Gly | Ile<br>200 | Gln | Lys | Asp | Arg | Val<br>205 | Asp | Lys | Ser |
| Ala | Val<br>210 | Gly | Phe | Asn | Glu | Met<br>215 | Glu | Ala | Pro | Thr | Thr<br>220 | Ala | Tyr | Lys | Lys |
| Thr | Thr | Pro | Ile | Glu | Ala | Ala | Ser | Ser | Gly | Ala | Arg | Gly | Leu | Lys | Ala |

```
225                         230                         235                         240
Lys  Phe  Glu  Ser  Met  Ala  Glu  Glu  Lys  Arg  Arg  Glu  Glu  Glu
               245                         250                         255

Lys  Ala  Gln  Gln  Val  Ala  Arg  Arg  Gln  Glu  Arg  Lys  Ala  Val  Thr
               260                         265                         270

Lys  Arg  Ser  Arg  Glu  Ala  Pro  Gln  Pro  Val  Ile  Ala  Met  Glu  Glu  Pro
               275                         280                         285

Ala  Val  Pro  Ala  Pro  Leu  Pro  Lys  Lys  Ile  Ser  Ser  Glu  Ala  Trp  Pro
     290                         295                         300

Pro  Val  Gly  Thr  Pro  Pro  Ser  Ser  Glu  Ser  Glu  Pro  Val  Arg  Thr  Ser
305                         310                         315                         320

Arg  Glu  His  Pro  Val  Pro  Leu  Leu  Pro  Ile  Arg  Gln  Thr  Leu  Pro  Glu
                    325                         330                         335

Asp  Asn  Glu  Glu  Pro  Pro  Ala  Leu  Pro  Pro  Arg  Thr  Leu  Glu  Gly  Leu
               340                         345                         350

Gln  Val  Glu  Glu  Glu  Pro  Val  Tyr  Glu  Ala  Glu  Pro  Glu  Pro  Glu  Pro
               355                         360                         365

Glu  Pro  Glu  Pro  Glu  Pro  Glu  Asn  Asp  Tyr  Glu  Asp  Val  Glu  Glu  Met
     370                         375                         380

Asp  Arg  His  Glu  Gln  Glu  Asp  Glu  Pro  Glu  Gly  Asp  Tyr  Glu  Glu  Val
385                         390                         395                         400

Leu  Glu  Pro  Glu  Asp  Ser  Ser  Phe  Ser  Ser  Ala  Leu  Ala  Gly  Ser  Ser
               405                         410                         415

Gly  Cys  Pro  Ala  Gly  Ala  Gly  Ala  Gly  Ala  Val  Ala  Leu  Gly  Ile  Ser
               420                         425                         430

Ala  Val  Ala  Leu  Tyr  Asp  Tyr  Gln  Gly  Glu  Gly  Ser  Asp  Glu  Leu  Ser
               435                         440                         445

Phe  Asp  Pro  Asp  Asp  Val  Ile  Thr  Asp  Ile  Glu  Met  Val  Asp  Glu  Gly
     450                         455                         460

Trp  Trp  Arg  Gly  Arg  Cys  His  Gly  His  Phe  Gly  Leu  Phe  Pro  Ala  Asn
465                         470                         475                         480

Tyr  Val  Lys  Leu  Leu  Glu
                    485
```

( 2 ) INFORMATION FOR SEQ ID NO:4:

( i ) SEQUENCE CHARACTERISTICS:
        ( A ) LENGTH: 546 amino acids
        ( B ) TYPE: amino acid
        ( C ) STRANDEDNESS: Not Relevant
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: HS1

( x i ) SEQUENCE DESCRIPTION: SEQ ID NO:4:

```
Met  Trp  Lys  Ala  Ser  Ala  Gly  His  Ala  Val  Ser  Ile  Thr  Gln  Asp  Asp
1                    5                         10                         15

Gly  Gly  Ala  Asp  Asp  Trp  Glu  Thr  Asp  Pro  Asp  Phe  Val  Asn  Asp  Val
               20                         25                         30

Ser  Glu  Lys  Glu  Gln  Arg  Trp  Gly  Ala  Lys  Thr  Val  Gln  Gly  Ser  Gly
               35                         40                         45
```

-continued

| | | | | | | | | | | | | | | |
|---|---|---|---|---|---|---|---|---|---|---|---|---|---|---|
|His|Gln|Glu|His|Ile|Asn|Ile|His|Lys|Leu|Arg|Glu|Asn|Val|Phe|Gln|
| |50| | | | |55| | | |60| | | | |
|Glu|His|Gln|Thr|Leu|Lys|Glu|Lys|Glu|Leu|Glu|Thr|Gly|Pro|Lys|Ala|
|65| | | | |70| | | |75| | | | |80|
|Ser|His|Gly|Tyr|Gly|Gly|Lys|Phe|Gly|Val|Glu|Gln|Asp|Arg|Met|Asp|
| | | | |85| | | |90| | | |95| | |
|Arg|Ser|Ala|Val|Gly|His|Glu|Tyr|Gln|Ser|Lys|Leu|Ser|Lys|His|Cys|
| | | |100| | | |105| | | |110| | |
|Ser|Gln|Val|Asp|Ser|Val|Arg|Gly|Phe|Gly|Lys|Phe|Gly|Val|Gln|
| | |115| | | |120| | | |125| | | |
|Met|Asp|Arg|Val|Asp|Gln|Ser|Ala|Val|Gly|Phe|Glu|Tyr|Gln|Gly|Lys|
| | |130| | | |135| | | |140| | | | |
|Thr|Glu|Lys|His|Ala|Ser|Gln|Lys|Asp|Tyr|Ser|Ser|Gly|Phe|Gly|Gly|
|145| | | | |150| | | |155| | | | |160|
|Arg|Tyr|Gly|Val|Gln|Ala|Asp|Arg|Val|Asp|Lys|Ser|Ala|Val|Gly|Phe|
| | | |165| | | |170| | | |175| | |
|Asp|Tyr|Gln|Gly|Lys|Thr|Glu|Lys|His|Glu|Ser|Gln|Lys|Asp|Tyr|Ser|
| | |180| | | |185| | | |190| | | |
|Lys|Gly|Phe|Gly|Gly|Lys|Tyr|Gly|Ile|Asp|Lys|Asp|Lys|Val|Asp|Lys|
| | |195| | | |200| | | |205| | | |
|Ser|Ala|Val|Gly|Phe|Glu|Tyr|Gln|Gly|Lys|Thr|Lys|His|Glu|Ser|
| |210| | | | |215| | | |220| | | | |
|Gln|Lys|Asp|Tyr|Val|Lys|Gly|Phe|Gly|Gly|Lys|Phe|Gly|Val|Gln|Thr|
|225| | | |230| | | |235| | | | | |240|
|Asp|Arg|Gln|Asp|Lys|Cys|Ala|Leu|Gly|Trp|Asp|His|Gln|Glu|Lys|Leu|
| | | |245| | | |250| | | |255| | |
|Gln|Leu|His|Glu|Ser|Gln|Lys|Asp|Tyr|Lys|Thr|Gly|Phe|Gly|Gly|Lys|
| | |260| | | |265| | | |270| | | |
|Phe|Gly|Val|Gln|Ser|Glu|Arg|Gln|Asp|Ser|Ser|Ala|Val|Gly|Phe|Asp|
| | |275| | | |280| | | |285| | | |
|Tyr|Lys|Glu|Arg|Leu|Ala|Lys|His|Glu|Pro|Gln|Gln|Asp|Tyr|Ala|Lys|
| |290| | | | |295| | | |300| | | | |
|Gly|Phe|Gly|Gly|Lys|Tyr|Gly|Val|Gln|Lys|Asp|Arg|Met|Asp|Lys|Asn|
|305| | | | |310| | | |315| | | | |320|
|Ala|Ser|Thr|Phe|Glu|Val|Val|Gln|Val|Pro|Ser|Ala|Tyr|Gln|Lys|
| | | |325| | | |330| | | |335| | |
|Thr|Val|Pro|Ile|Glu|Ala|Val|Thr|Ser|Lys|Thr|Ser|Asn|Ile|Arg|Ala|
| | |340| | | |345| | | |350| | | |
|Asn|Phe|Glu|Asn|Leu|Ala|Lys|Glu|Arg|Glu|Gln|Glu|Asp|Arg|Arg|Lys|
| |355| | | | |360| | | |365| | | | |
|Ala|Glu|Ala|Glu|Arg|Ala|Gln|Arg|Met|Ala|Lys|Glu|Arg|Gln|Glu|Gln|
|370| | | | |375| | | |380| | | | | |
|Glu|Glu|Ala|Arg|Arg|Lys|Leu|Glu|Glu|Gln|Ala|Arg|Ala|Lys|Lys|Gln|
|385| | | |390| | | |395| | | | | |400|
|Thr|Pro|Pro|Ala|Ser|Pro|Ser|Pro|Gln|Pro|Ile|Glu|Asp|Arg|Pro|Pro|
| | | |405| | | |410| | | |415| | |
|Ser|Ser|Pro|Ile|Tyr|Glu|Asp|Ala|Ala|Pro|Phe|Lys|Ala|Glu|Pro|Ser|
| | |420| | | |425| | | |430| | | |
|Tyr|Arg|Gly|Ser|Glu|Pro|Glu|Pro|Tyr|Ser|Ile|Glu|Ala|Ala|Gly|
| | |435| | | |440| | | |445| | | | |
|Ile|Pro|Glu|Ala|Gly|Ser|Gln|Gln|Gly|Leu|Thr|Tyr|Thr|Ser|Glu|Pro|
| |450| | | | |455| | | |460| | | | |
|Val|Tyr|Glu|Thr|Thr|Glu|Ala|Pro|Gly|His|Tyr|Gln|Ala|Glu|Asp|Asp|

```
         465                  470                    475                      480
Thr  Tyr  Asp  Gly  Tyr  Glu  Ser  Asp  Leu  Gly  Ile  Thr  Ala  Ile  Ala  Leu
                         485                    490                     495
Tyr  Asp  Tyr  Gln  Ala  Ala  Gly  Asp  Asp  Glu  Ile  Ser  Phe  Asp  Pro  Asp
                    500                    505                    510
Asp  Ile  Ile  Thr  Asn  Ile  Glu  Met  Ile  Asp  Asp  Gly  Trp  Trp  Arg  Gly
               515                    520                    525
Val  Cys  Lys  Gly  Arg  Tyr  Gly  Leu  Phe  Pro  Ala  Asn  Tyr  Val  Glu  Leu
     530                    535                         540
Arg  Gln
545
```

( 2 ) INFORMATION FOR SEQ ID NO:5:

( i ) SEQUENCE CHARACTERISTICS:
        ( A ) LENGTH: 37 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:5:

```
Glu  His  Asp  Ile  Leu  Lys  Lys  Lys  Glu  Leu  Glu  Ser  Gly  Pro  Lys  Ala
1                    5                         10                        15
Ser  His  Gly  Tyr  Gly  Gly  Gln  Phe  Gly  Val  Glu  Arg  Asp  Arg  Met  Asp
               20                        25                   30
Lys  Ser  Ala  Val  Gly
               35
```

( 2 ) INFORMATION FOR SEQ ID NO:6:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
His  Glu  Tyr  Val  Ala  Asp  Val  Glu  Lys  His  Ser  Ser  Gln  Thr  Asp  Ala
1                    5                         10                        15
Ala  Arg  Gly  Phe  Gly  Gly  Lys  Tyr  Gly  Val  Glu  Arg  Asp  Arg  Ala  Asp
               20                        25                   30
Lys  Ser  Ala  Val  Gly
               35
```

( 2 ) INFORMATION FOR SEQ ID NO:7:

( i ) SEQUENCE CHARACTERISTICS:
        ( A ) LENGTH: 37 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:7:

```
Phe  Asp  Tyr  Lys  Gly  Glu  Val  Glu  Lys  His  Ala  Ser  Gln  Lys  Asp  Tyr
1                    5                         10                        15
Ser  His  Gly  Phe  Gly  Gly  Arg  Tyr  Gly  Val  Glu  Lys  Asp  Lys  Arg  Asp
               20                        25                   30
```

Lys Ala Ala Leu Gly
            35

(2) INFORMATION FOR SEQ ID NO:8:

(i) SEQUENCE CHARACTERISTICS:
        (A) LENGTH: 37 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:8:

Tyr Asp Tyr Lys Gly Glu Thr Glu Lys His Glu Ser Gln Arg Asp Tyr
1               5                   10                  15
Ala Lys Gly Phe Gly Gly Gln Tyr Gly Ile Gln Lys Asp Arg Val Asp
            20                  25                  30
Lys Ser Ala Val Gly
            35

(2) INFORMATION FOR SEQ ID NO:9:

(i) SEQUENCE CHARACTERISTICS:
        (A) LENGTH: 28 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:9:

Met Ser Arg Glu Val Gln Gln Pro Ser Met Pro Val Glu Glu Pro Ala
1               5                   10                  15
Ala Pro Ala Gln Leu Pro Lys Lys Ile Ser Ser Glu
            20                  25

(2) INFORMATION FOR SEQ ID NO:10:

(i) SEQUENCE CHARACTERISTICS:
        (A) LENGTH: 34 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:10:

Val Trp Pro Pro Ala Glu Ser His Leu Pro Pro Glu Ser Gln Pro Val
1               5                   10                  15
Arg Ser Arg Arg Glu Tyr Pro Val Pro Ser Leu Pro Thr Arg Gln Ser
            20                  25                  30
Pro Leu (2) INFORMATION FOR SEQ ID NO:11:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:11:

Gln Asn His Leu Glu Asp Asn Glu Glu Pro Pro Ala Leu Pro Pro Arg
1               5                   10                  15

Thr Pro (2) INFORMATION FOR SEQ ID NO:12:

(i) SEQUENCE CHARACTERISTICS:
        (A) LENGTH: 36 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:12:

```
Glu Gly Leu Gln Val Val Glu Glu Pro Val Tyr Glu Ala Ala Pro Glu
 1               5                  10                  15
Leu Glu Pro Glu Pro Glu Pro Asp Tyr Glu Pro Glu Pro Glu Thr Glu
                20                  25                  30
Pro Asp Tyr Glu
            35
```

(2) INFORMATION FOR SEQ ID NO:13:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Val Trp Pro Pro Ala Glu Ser His Leu Pro Pro Glu Ser Gln Pro Val
 1               5                  10                  15
Arg Thr Arg Arg Glu Tyr Pro Val Pro Ser Leu Pro Thr Arg Gln Ser
                20                  25                  30
Pro Leu
```

(2) INFORMATION FOR SEQ ID NO:14:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Val Trp Pro Pro Ala Glu Ser His Leu Pro Pro Glu Ser Gln Pro Val
 1               5                  10                  15
Arg Ser Arg Arg Glu Tyr Pro Val Pro Leu Leu Pro Thr Arg Gln Ser
                20                  25                  30
Pro Leu
```

(2) INFORMATION FOR SEQ ID NO:15:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Val  Trp  Pro  Pro  Ala  Glu  Ser  His  Leu  Pro  Pro  Glu  Ser  Gln  Pro  Val
1                   5                        10                      15

Arg  Ser  Arg  Arg  Glu  Tyr  Pro  Val  Pro  Ser  Leu  Pro  Ile  Arg  Gln  Ser
              20                        25                   30

Pro  Leu
```

( 2 ) INFORMATION FOR SEQ ID NO:16:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Val  Trp  Pro  Pro  Ala  Glu  Ser  His  Leu  Pro  Pro  Glu  Ser  Gln  Pro  Val
1                   5                        10                      15

Arg  Ser  Arg  Arg  Glu  Tyr  Pro  Val  Pro  Ser  Leu  Pro  Thr  Arg  Gln  Thr
              20                        25                   30

Pro  Leu
```

( 2 ) INFORMATION FOR SEQ ID NO:17:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Val  Trp  Pro  Pro  Ala  Glu  Ser  His  Leu  Pro  Pro  Glu  Ser  Gln  Pro  Val
1                   5                        10                      15

Arg  Ser  Arg  Arg  Glu  Tyr  Pro  Val  Pro  Ser  Leu  Pro  Thr  Arg  Gln  Ser
              20                        25                   30
```

( 2 ) INFORMATION FOR SEQ ID NO:18:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
Val  Trp  Pro  Pro  Ala  Glu  Ser  His  Leu  Pro  Pro  Glu  Ser  Gln  Pro  Val
1                   5                        10                      15

Arg  Thr  Arg  Arg  Glu  Tyr  Pro  Val  Pro  Leu  Leu  Pro  Ile  Arg  Gln  Thr
              20                        25                   30

Pro  Leu
```

( 2 ) INFORMATION FOR SEQ ID NO:19:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

Val Trp Pro Pro Ala Glu Ser His Leu Pro Pro Glu Ser Gln Pro Val
1               5                       10                      15

Arg Ser Arg Arg Glu Tyr Pro Val Pro Leu Leu Pro Thr Arg Gln Thr
                20                      25                  30

Pro Leu ( 2 ) INFORMATION FOR SEQ ID NO:20:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

Val Trp Pro Pro Ala Glu Ser His Pro Pro Glu Ser Gln Pro Val Arg
1               5                       10                      15

Ser Arg Arg Glu Tyr Pro Val Pro Leu Leu Pro Ile Arg Gln Ser Leu
                20                      25                  30

( 2 ) INFORMATION FOR SEQ ID NO:21:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

Val Trp Pro Pro Val Gly Thr Pro Pro Ser Ser Glu Ser Gln Pro Val
1               5                       10                      15

Arg Ser Arg Arg Glu Tyr Pro Val Pro Ser Leu Pro Thr Arg Gln Ser
                20                      25                  30

Pro Leu ( 2 ) INFORMATION FOR SEQ ID NO:22:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

Gln Asn His Glu Asp Asn Glu Glu Pro Pro Ala Leu Pro Pro Arg Thr
1               5                       10                      15

Pro Glu Gly Leu Gln Val Val Glu
                20

( 2 ) INFORMATION FOR SEQ ID NO:23:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

Gln Asn His Leu Glu Asp Asn Glu Glu Pro Pro Ala Leu Pro Pro Arg
1               5                   1 0                  1 5

Thr Glu Gly Leu Gln Val Val Glu
            2 0

( 2 ) INFORMATION FOR SEQ ID NO:24:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

Gln Asn His Glu Asp Asn Glu Glu Pro Pro Ala Leu Pro Pro Arg Thr
1               5                   1 0                  1 5

Glu Gly Leu Gln Val Val Glu
            2 0

( 2 ) INFORMATION FOR SEQ ID NO:25:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

Gln Asn His Leu Glu Asp Asn Glu Glu Pro Pro Ala Leu Pro Pro Arg
1               5                   1 0                  1 5

Ser Pro Glu Gly Leu Gln Val Val Glu
            2 0                  2 5

( 2 ) INFORMATION FOR SEQ ID NO:26:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

Gln Asn His Leu Glu Asp Asn Glu Glu Pro Pro Ala Ser Pro Pro Arg
1               5                   1 0                  1 5

Thr Pro Glu Gly Leu Gln Val Val Glu
            2 0                  2 5

( 2 ) INFORMATION FOR SEQ ID NO:27:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

His Leu Glu Asp Asn Glu Glu Pro Pro Ala Leu Pro Pro Arg Thr Pro
1               5                   1 0                  1 5

Glu Gly Leu Gln Val Val Glu
            20

(2) INFORMATION FOR SEQ ID NO:28:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

His Glu Asp Asn Glu Glu Pro Pro Ala Leu Pro Pro Arg Thr Glu Gly
1               5                   10                  15
Ser Gln Val Val Glu
            20

(2) INFORMATION FOR SEQ ID NO:29:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

Ala Ile Ala Leu Tyr Asp Tyr Gln Gly Glu Gly Ser Asp Glu Leu Ser
1               5                   10                  15
Phe Asp Pro Asp Asp Ile Ile Thr Asp Ile Glu Met Val Asp Glu Gly
            20                  25                  30
Trp Trp Arg Gly Gln Cys Arg Gly His Phe Gly Leu Phe Pro Ala Asn
            35                  40                  45
Tyr Val Lys Leu Leu
            50

(2) INFORMATION FOR SEQ ID NO:30:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

Ala Val Ala Leu Tyr Asp Tyr Gln Gly Glu Gly Ser Asp Glu Leu Ser
1               5                   10                  15
Phe Asp Pro Asp Asp Ile Ile Thr Asp Ile Glu Met Val Asp Glu Gly
            20                  25                  30
Trp Trp Arg Gly Gln Cys Arg Gly His Phe Gly Leu Phe Pro Ala Asn
            35                  40                  45
Tyr Val Lys Leu Leu
            50

(2) INFORMATION FOR SEQ ID NO:31:

(i) SEQUENCE CHARACTERISTICS:
        (A) LENGTH: 53 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO:31:

```
Ala Ile Ala Ser Tyr Asp Tyr Gln Gly Glu Gly Ser Asp Glu Leu Ser
1               5                   10                  15
Phe Asp Pro Asp Asp Ile Ile Thr Asp Ile Glu Met Val Asp Glu Gly
            20                  25                  30
Trp Trp Arg Gly Gln Cys Arg Gly His Phe Gly Leu Phe Pro Ala Asn
        35                  40                  45
Tyr Val Lys Leu Leu
    50
```

(2) INFORMATION FOR SEQ ID NO:32:

(i) SEQUENCE CHARACTERISTICS:
(A) LENGTH: 53 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:32:

```
Ala Ile Ala Leu Tyr Asp Tyr Gln Gly Glu Gly Ser Asp Glu Leu Ser
1               5                   10                  15
Phe Asp Pro Asp Asp Ile Ile Ile Asp Ile Glu Met Val Asp Glu Gly
            20                  25                  30
Trp Trp Arg Gly Gln Cys Arg Gly His Phe Gly Leu Phe Pro Ala Asn
        35                  40                  45
Tyr Val Lys Leu Leu
    50
```

(2) INFORMATION FOR SEQ ID NO:33:

(i) SEQUENCE CHARACTERISTICS:
(A) LENGTH: 53 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:33:

```
Ala Ile Ala Leu Tyr Asp Tyr Gln Gly Glu Gly Ser Asp Glu Leu Ser
1               5                   10                  15
Phe Asp Pro Asp Asp Val Ile Thr Asp Ile Glu Met Val Asp Glu Gly
            20                  25                  30
Trp Trp Arg Gly Gln Cys Arg Gly His Phe Gly Leu Phe Pro Ala Asn
        35                  40                  45
Tyr Val Lys Leu Leu
    50
```

(2) INFORMATION FOR SEQ ID NO:34:

(i) SEQUENCE CHARACTERISTICS:
(A) LENGTH: 53 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:34:

Ala Ile Ala Leu Tyr Asp Tyr Gln Gly Glu Gly Thr Asp Glu Leu Ser
1               5                           10                          15

Phe Asp Pro Asp Asp Ile Ile Thr Asp Ile Glu Met Val Asp Glu Gly
                20                      25                      30

Trp Trp Arg Gly Gln Cys Arg Gly His Phe Gly Leu Phe Pro Ala Asn
            35                      40                  45

Tyr Val Lys Leu Leu
        50

( 2 ) INFORMATION FOR SEQ ID NO:35:

( i ) SEQUENCE CHARACTERISTICS:
        ( A ) LENGTH: 53 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:35:

Ala Ile Ala Leu Tyr Asp Tyr Gln Gly Glu Gly Ser Asp Glu Leu Ser
1               5                           10                          15

Phe Asp Pro Asp Asp Ile Ile Thr Asp Ile Glu Met Val Asp Glu Gly
                20                      25                      30

Trp Trp Arg Gly Arg Cys His Gly His Phe Gly Leu Phe Pro Ala Asn
            35                      40                  45

Tyr Val Lys Leu Leu
        50

( 2 ) INFORMATION FOR SEQ ID NO:36:

( i ) SEQUENCE CHARACTERISTICS:
        ( A ) LENGTH: 54 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:36:

Ala Ile Ala Leu Tyr Asp Tyr Gln Gly Glu Gly Ser Asp Glu Leu Ser
1               5                           10                          15

Phe Asp Pro Asp Asp Ile Ile Thr Asp Ile Glu Met Val Asp Glu Gly
                20                      25                      30

Trp Trp Arg Gly Gln Cys Arg Gly His Phe Gly Leu Phe Pro Ala Asn
            35                      40                  45

Tyr Val Lys Leu Leu Glu
        50

( 2 ) INFORMATION FOR SEQ ID NO:37:

( i ) SEQUENCE CHARACTERISTICS:
        ( A ) LENGTH: 53 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:37:

Ala Ile Ala Leu Tyr Asp Tyr Gln Ala Ala Gly Ser Asp Glu Leu Ser
1               5                           10                          15

Phe Asp Pro Asp Asp Ile Ile Thr Asp Ile Glu Met Val Asp Glu Gly

```
                          20                      25                        30
Trp Trp Arg Gly Gln Cys Arg Gly His Phe Gly Leu Phe Pro Ala Asn
            35                      40                  45

Tyr Val Lys Leu Leu
    50
```

( 2 ) INFORMATION FOR SEQ ID NO:38:

( i ) SEQUENCE CHARACTERISTICS:
        ( A ) LENGTH: 54 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:38:

```
Ala Val Ala Leu Tyr Asp Tyr Gln Gly Glu Gly Ser Asp Glu Leu Ser
1               5                   10                  15
Phe Asp Pro Asp Asp Val Ile Thr Asp Ile Glu Met Val Asp Glu Gly
            20                  25                  30
Trp Trp Arg Gly Gln Cys Arg Gly His Phe Gly Leu Phe Pro Ala Asn
            35                      40                  45
Tyr Val Lys Leu Leu Glu
    50
```

( 2 ) INFORMATION FOR SEQ ID NO:39:

( i ) SEQUENCE CHARACTERISTICS:
        ( A ) LENGTH: 53 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:39:

```
Ala Ile Ala Leu Tyr Asp Tyr Gln Gly Glu Gly Thr Asp Glu Leu Thr
1               5                   10                  15
Phe Asp Pro Asp Asp Ile Thr Ile Asp Ile Glu Met Val Asp Glu Gly
            20                  25                  30
Trp Trp Arg Gly Gln Cys Arg Gly His Phe Gly Leu Phe Pro Ala Asn
            35                      40                  45
Tyr Val Lys Leu Leu
    50
```

( 2 ) INFORMATION FOR SEQ ID NO:40:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PCR primer"

( x i ) SEQUENCE DESCRIPTION: SEQ ID NO:40:

```
GGGGGGATCC ATGGGCTGTG TCTGCAGCTC AAACCCT                          37
```

( 2 ) INFORMATION FOR SEQ ID NO:41:

( i ) SEQUENCE CHARACTERISTICS:
        ( A ) LENGTH: 37 base pairs
        ( B ) TYPE: nucleic acid ( C ) STRANDEDNESS: single
( D ) TOPOLOGY: linear ( i i ) MOLECULE TYPE: other nucleic acid
( A ) DESCRIPTION: /desc ="PCR primer"

( x i ) SEQUENCE DESCRIPTION: SEQ ID NO:41:

GGGGGAATTC TCAAGGCTGG GGCTGGTACT GGCCCTC 37

( 2 ) INFORMATION FOR SEQ ID NO:42:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="PCR primer"

( x i ) SEQUENCE DESCRIPTION: SEQ ID NO:42:

GGGGGGATCC CAAGACAACC TGGTTATCGC CCTGCAC 37

( 2 ) INFORMATION FOR SEQ ID NO:43:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="PCR primer"

( x i ) SEQUENCE DESCRIPTION: SEQ ID NO:43:

GGGGGAATTC TCAAGGTTCA GGCTCCAGGC TGTTTGC 37

( 2 ) INFORMATION FOR SEQ ID NO:44:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="PCR primer"

( x i ) SEQUENCE DESCRIPTION: SEQ ID NO:44:

GGGGGAATTC TGGTTCTTCA AGAATCTGAG 30

( 2 ) INFORMATION FOR SEQ ID NO:45:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="PCR primer"

( x i ) SEQUENCE DESCRIPTION: SEQ ID NO:45:

GGGGGAATTC TCACCACCAT GGTTTCTGGG 30

( 2 ) INFORMATION FOR SEQ ID NO:46:

( i ) SEQUENCE CHARACTERISTICS:
( A ) LENGTH: 33 base pairs
( B ) TYPE: nucleic acid ( C ) STRANDEDNESS: single
( D ) TOPOLOGY: linear ( i i ) MOLECULE TYPE: other nucleic acid
( A ) DESCRIPTION: /desc ="PCR primer"

( x i ) SEQUENCE DESCRIPTION: SEQ ID NO:46:

GGGGGGATCC GAGGACGAAT GGGAAGTTCC CAG 33

( 2 ) INFORMATION FOR SEQ ID NO:47:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="PCR primer"

( x i ) SEQUENCE DESCRIPTION: SEQ ID NO:47:

GGGGGGGAAT TCTCAAGGCT GGGGCTGGTA CTGGCCCTC 39

( 2 ) INFORMATION FOR SEQ ID NO:48:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="PCR primer"

( x i ) SEQUENCE DESCRIPTION: SEQ ID NO:48:

GGGGGGATCC ATGGAGGCCC CAACCACGGC GTA 33

( 2 ) INFORMATION FOR SEQ ID NO:49:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="PCR primer"

( x i ) SEQUENCE DESCRIPTION: SEQ ID NO:49:

GGGGGGATCC GAGCCAGTGT ACGAAGCAGC A 31

( 2 ) INFORMATION FOR SEQ ID NO:50:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="PCR primer"

( x i ) SEQUENCE DESCRIPTION: SEQ ID NO:50:

GGGGGATCCT ATGAGGATGT TGGGGAGTTA G 31

( 2 ) INFORMATION FOR SEQ ID NO:51:

( i ) SEQUENCE CHARACTERISTICS:
( A ) LENGTH: 31 base pairs
( B ) TYPE: nucleic acid ( C ) STRANDEDNESS: single
( D ) TOPOLOGY: linear ( i i ) MOLECULE TYPE: other nucleic acid
( A ) DESCRIPTION: /desc ="PCR primer"

( x i ) SEQUENCE DESCRIPTION: SEQ ID NO:51:

GGGGGGATCC GCTATAGCCC TGTATGATTA C     31

( 2 ) INFORMATION FOR SEQ ID NO:52:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="PCR primer"

( x i ) SEQUENCE DESCRIPTION: SEQ ID NO:52:

GGGGGGATCC ATGAGCCGAG AAGTCCAGCA G     31

( 2 ) INFORMATION FOR SEQ ID NO:53:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="PCR primer"

( x i ) SEQUENCE DESCRIPTION: SEQ ID NO:53:

GGGGGGATCC GTCTGGCCTC CAGCAGAGAG T     31

( 2 ) INFORMATION FOR SEQ ID NO:54:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="PCR primer"

( x i ) SEQUENCE DESCRIPTION: SEQ ID NO:54:

GGGGGGATCC CAGAATCACT TGGAGGACAA C     31

( 2 ) INFORMATION FOR SEQ ID NO:55:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="PCR primer"

( x i ) SEQUENCE DESCRIPTION: SEQ ID NO:55:

GGGGGGATCC GAAGGCCTCC AGGTGGTGGA AG     32

( 2 ) INFORMATION FOR SEQ ID NO:56:

( i ) SEQUENCE CHARACTERISTICS:
( A ) LENGTH: 33 base pairs
( B ) TYPE: nucleic acid (C) STRANDEDNESS: single
(D) TOPOLOGY: linear (i i) MOLECULE TYPE: other nucleic acid
(A) DESCRIPTION: /desc ="PCR primer"

(x i) SEQUENCE DESCRIPTION: SEQ ID NO:56:

GGGGGAATTC TCATTAGAGG AGCTTGACAT AGT 33

(2) INFORMATION FOR SEQ ID NO:57:

(i) SEQUENCE CHARACTERISTICS:
(A) LENGTH: 30 base pairs
(B) TYPE: nucleic acid
(C) STRANDEDNESS: single
(D) TOPOLOGY: linear (i i) MOLECULE TYPE: other nucleic acid
(A) DESCRIPTION: /desc ="PCR primer"

(x i) SEQUENCE DESCRIPTION: SEQ ID NO:57:

GGGGAATTCC TAGGCTATAG CAGAGATCCC 30

(2) INFORMATION FOR SEQ ID NO:58:

(i) SEQUENCE CHARACTERISTICS:
(A) LENGTH: 32 base pairs
(B) TYPE: nucleic acid
(C) STRANDEDNESS: single
(D) TOPOLOGY: linear (i i) MOLECULE TYPE: other nucleic acid
(A) DESCRIPTION: /desc ="PCR primer"

(x i) SEQUENCE DESCRIPTION: SEQ ID NO:58:

GGGGGAATTC ATTCCACCAC CTGGAGGCCT TC 32

(2) INFORMATION FOR SEQ ID NO:59:

(i) SEQUENCE CHARACTERISTICS:
(A) LENGTH: 32 base pairs
(B) TYPE: nucleic acid
(C) STRANDEDNESS: single
(D) TOPOLOGY: linear (i i) MOLECULE TYPE: other nucleic acid
(A) DESCRIPTION: /desc ="PCR primer"

(x i) SEQUENCE DESCRIPTION: SEQ ID NO:59:

GGGGGAATTC ACAATGGAGA CTGCCTCGTG GG 32

(2) INFORMATION FOR SEQ ID NO:60:

(i) SEQUENCE CHARACTERISTICS:
(A) LENGTH: 32 base pairs
(B) TYPE: nucleic acid
(C) STRANDEDNESS: single
(D) TOPOLOGY: linear (i i) MOLECULE TYPE: other nucleic acid
(A) DESCRIPTION: /desc ="PCR primer"

(x i) SEQUENCE DESCRIPTION: SEQ ID NO:60:

GGGGGAATTC ACTGCTGGAC TTCTCGGCTC AT 32

(2) INFORMATION FOR SEQ ID NO:61:

(i) SEQUENCE CHARACTERISTICS:
(A) LENGTH: 32 base pairs
(B) TYPE: nucleic acid (C) STRANDEDNESS: single
(D) TOPOLOGY: linear (ii) MOLECULE TYPE: other nucleic acid
(A) DESCRIPTION: /desc ="PCR primer"

(xi) SEQUENCE DESCRIPTION: SEQ ID NO:61:

GGGGGAATTC ACTCTGAGGA GATCTTCTTG GG 32

(2) INFORMATION FOR SEQ ID NO:62:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="PCR primer"

(xi) SEQUENCE DESCRIPTION: SEQ ID NO:62:

GGGGGAATTC ACAATGGAGA CTGCCTCGTG GG 32

(2) INFORMATION FOR SEQ ID NO:63:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="PCR primer"

(xi) SEQUENCE DESCRIPTION: SEQ ID NO:63:

GGGGGAATTC ATTCCACCAC CTGGAGGCCT TC 32

(2) INFORMATION FOR SEQ ID NO:64:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="PCR primer"

(xi) SEQUENCE DESCRIPTION: SEQ ID NO:64:

GGGGGAATTC ACTCATAGTC AGGCTCTGTC TC 32

(2) INFORMATION FOR SEQ ID NO:65:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: other nucleic acid
(A) DESCRIPTION: /desc ="PCR primer"

(xi) SEQUENCE DESCRIPTION: SEQ ID NO:65:

AGTCTCCCTC TGCATCC 17

(2) INFORMATION FOR SEQ ID NO:66:

(i) SEQUENCE CHARACTERISTICS:
(A) LENGTH: 38 base pairs
(B) TYPE: nucleic acid ( C ) STRANDEDNESS: single
( D ) TOPOLOGY: linear ( i i ) MOLECULE TYPE: other nucleic acid
( A ) DESCRIPTION: /desc ="PCR primer"

( x i ) SEQUENCE DESCRIPTION: SEQ ID NO:66:

| CACACACAGG | CCACGCGTCG | ACTAGTACGG | GGGGGGGG | | | 38 |
|---|---|---|---|---|---|---|

( 2 ) INFORMATION FOR SEQ ID NO:67:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="PCR primer"

( x i ) SEQUENCE DESCRIPTION: SEQ ID NO:67:

| CACACACAGC | CAACAGCACT | CTTATCCAC | | | | 29 |
|---|---|---|---|---|---|---|

( 2 ) INFORMATION FOR SEQ ID NO:68:

( i ) SEQUENCE CHARACTERISTICS:
( A ) LENGTH: 1458 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:68:

| ATGTGGAAGT | CTGTAGTGGG | GCATGATGTA | TCGGTTTCCG | TGGAGACCCA | GGGTGATGAC | 60 |
|---|---|---|---|---|---|---|
| TGGGATACAG | ACCCTGACTT | TGTGAATGAC | ATCTCCGAGA | AGGAGCAACG | GTGGGGAGCC | 120 |
| AAGACCATTG | AGGGCTCTGG | ACGCACAGAG | CACATCAACA | TCCACCAGCT | GAGGAACAAA | 180 |
| GTGTCAGAGG | AGCACGACAT | CCTCAAGAAG | AAGGAGCTGG | AATCGGGGCC | TAAGGCATCC | 240 |
| CATGGCTATG | GCGGTCAGTT | TGGAGTGGAG | AGAGACCGGA | TGGACAAGAG | TGCCGTGGGC | 300 |
| CACGAGTATG | TTGCTGATGT | GGAGAAACAC | TCATCTCAGA | CTGATGCCGC | CAGAGGCTTT | 360 |
| GGGGGCAAAT | ATGGAGTTGA | GAGGGACCGG | GCAGACAAGT | CAGCGGTGGG | CTTTGACTAC | 420 |
| AAAGGAGAAG | TGGAAAAGCA | TGCATCTCAG | AAAGATTACT | CTCATGGCTT | TGGTGGCCGC | 480 |
| TACGGGGTAG | AGAAGGATAA | ACGGGACAAA | GCAGCCCTGG | GATACGACTA | CAAAGGAGAG | 540 |
| ACGGAGAAGC | ACGAGTCTCA | GAGAGATTAT | GCCAAGGGCT | TTGGTGGCCA | ATATGGAATC | 600 |
| CAGAAAGACC | GAGTGGATAA | GAGTGCTGTT | GGCTTCAATG | AAATGGAGGC | CCCAACCACG | 660 |
| GCGTATAAGA | AGACAACACC | CATAGAAGCT | GCTTCCAGTG | GTGCCCGTGG | GCTGAAGGCA | 720 |
| AAATTTGAGT | CCCTGGCTGA | GGAGAAGAGG | AAGCGAGAGG | AAGAAGAGAA | GGCACAGCAG | 780 |
| ATGGCCAGGC | AGCAACAGGA | GCGAAAGGCT | GTGGTAAAGA | TGAGCCGAGA | AGTCCAGCAG | 840 |
| CCATCCATGC | CTGTGGAAGA | GCCAGCGGCA | CCAGCCCAGT | TGCCCAAGAA | GATCTCCTCA | 900 |
| GAGGTCTGGC | CTCCAGCAGA | GAGTCACCTA | CCGCCAGAGT | CTCAGCCAGT | GAGAAGCAGA | 960 |
| AGGGAATACC | CTGTGCCCTC | TCTGCCCACG | AGGCAGTCTC | CATTGCAGAA | TCACTTGGAG | 1020 |
| GACAACGAGG | AGCCCCCAGC | TCTGCCCCCT | AGGACCCAG | AAGGCCTCCA | GGTGGTGGAA | 1080 |
| GAGCCAGTGT | ACGAAGCAGC | ACCCGAGCTG | GAGCCGGAGC | CAGAGCCTGA | CTATGAGCCA | 1140 |
| GAGCCAGAGA | CAGAGCCTGA | CTATGAGGAT | GTTGGGGAGT | TAGATCGGCA | GGATGAGGAT | 1200 |
| GCAGAGGGAG | ACTATGAGGA | TGTGCTGGAG | CCCGAGGACA | CCCCTTCTCT | GTCCTACCAA | 1260 |

```
GCTGGACCCT CAGCTGGGGC TGGTGGTGCG GGGATCTCTG CTATAGCCCT GTATGATTAC      1320

CAAGGAGAGG GAAGCGATGA GCTTTCCTTT GATCCAGATG ACATCATCAC TGACATTGAG      1380

ATGGTGGATG AAGGCTGGTG GCGGGGCCAA TGCCGTGGCC ACTTTGGACT TTTCCCTGCA      1440

AACTATGTCA AGCTCCTC                                                    1458
```

LCK BINDING PROTEIN

This application is a continuation of U.S. Ser. No. 08/362,715, filed Dec. 23, 1994, abandoned.

FIELD OF THE INVENTION

The present invention relates to Lck tyrosine kinase and its role in the differentiation of T-cells, particularly to identification and modulation of the Lck pathway, and specifically to murine Lck binding protein ("LckBP1"), cDNA encoding for LckBP1, and methods of use therefor.

BACKGROUND INFORMATION

The Lck tyrosine kinase molecule ($p56^{lck}$), a lymphocyte specific, non-receptor type src-family protein kinase, plays a key role during the activation and early differentiation of T cells. This role has been described in the literature as follows. Defective TCR-mediated signaling observed in a lck mutant human Jurkat cell line was restored upon transfection of the cell with an intact gene (Straus and Weiss, 1992 Cell, 70, 585–593), suggesting a requirement for lck molecule in TCR-mediated signaling. Lck-deficient mice showed a dramatic reduction in double-positive ($CD4^+$ $CD8^+$) thymocytes, and no detectable single-positive thymocytes (Molina et al., 1992 Nature, 357, 161–164). Overexpression of a catalytically inactive version of Lck resulted in the maturational arrest of T cells at the $G_0/G_1$ thymoblast stage (Levin et al., 1993 EMBO J., 12, 1671–1680).

Lck has been shown to associate physically and functionally with several molecules, such as CD4 and CD8 in the TCR complex (Shaw et al., 1989, Cell, 59, 627–636) and the interleukin-2 receptor β chain (Hatakeyama et al., 1991 Science, 252, 1523–1528). The function of Lck is modulated by C-terminal Src kinase (CSK; Bergman et al., 1992 EMBO J., 11, 2919–2924; Chow et al., 1993 Nature, 365, 156–160; Autero et al., 1994 Mol. Cell. Biol., 14, 1308–1321) and tyrosine phosphatase CD45 (Mustelin and Altman, 1990 Oncogene, 5, 809–813; Mustelin et al., 1989 Proc. Natl. Acad. Sci. USA, 86, 6302–6306; Ostergaard et al., 1989 Proc. Natl. Acad. Sci. USA, 86, 8959–8963; Autero et al., 1994 Mol. Cell. Biol., 14, 1308–1321; reviewed by Mustelin and Burn, 1993 Trends Biochem. Sci., 18, 215–220).

Like other src-family protein kinases, Lck consists of three domains: the kinase, the Src homology region 2 ("SH2") and the Src homology region 3 ("SH3") domains. The SH2 domain of Lck has been reported to bind to tyrosine phosphorylated CD45 (Autero et al., 1994) and to ZAP-70 (Duplay et al., 1994 J. Exp. Med., 179, 1163–1172). ZAP-70 deficiency has been correlated with immunodeficiency in patients (Arpaia et al., Cell 76, 947–958, 1994). Since ZAP-70 binds to Lck and ZAP-70 deficiency is related to immunodeficiency, Lck binding is predictive of immunomodulatory activity for a binding protein.

The SH3 domain of Lck has been shown to associate with phosphatidylinositol (PI) 3-kinase (Prasad et al., 1993 Mol. Cell. Biol., 13, 7708–7717; Vogel and Fujita, 1993 Mol. Cell. Biol., 13, 7408–7417) and with p120 (Reedquist et al., 1994 Proc. Natl. Acad. Sci. USA, 91, 4135–4139); it is reported to participate in signal transduction or in membrane-cytoskelton interactions. Previous reports showed that the SH3 domain mediates protein-protein interactions via binding to proline-rich regions, such as those in 3BP-1,2 (Ren et al., 1993 Science, 259, 1157–1161), Sos (Li et al., 1993 Nature, 363, 85–88; Rozakis-Adcock et al., 1993 Nature, 363, 83–85), and Abl (Ren et al., 1994 Genes & Develop., 8, 783–795). Deletion or mutation of the SH3 domain usually activates the transforming potential of non-receptor type tyrosine kinases, suggesting that the SH3 domain negatively regulates the transforming activities of such proteins (Jackson and Baltimore, 1989 EMBO J., 8, 449–456; Hirai and Vermus 1990 Mol. Cell. Biol., 10, 1307–1318; Kato et al., 1986 Mol. Cell. Biol., 6, 4155–4160; Potts et al., 1998 Oncogene Res., 3, 343–355; Franz et al., 1989 EMBO J., 8, 137–147; Seidel-Dugan et al., 1992 Mol. Cell. Biol., 12, 1835–1845).

Proteins that directly associate with the SH3 domain in the c-abl proto-oncogene have been identified by the West-Western method (Cicchetti et al., 1992 Science, 257, 803–806), a method that allows direct isolation of genes encoding proteins that associate with target species such as the SH3 proteins. This procedure involves induction of proteins from a λgt 11 cDNA expression library and screening the proteins on nitrocellulose membranes using a protein or peptide probe. Previously with this method, several proteins have been identified that associate with intracellular signaling molecules or transcriptional factors, such as Max associating with Myc (Blackwood and Hisenman, 1991 Science, 251, 1211–1217), and 3BP-1 with the SH3 region of Abl (Cicchetti et al., 1992). These methods were employed in the present invention.

Alteration, preferably reduction, of the interaction of protein-tyrosine kinases and T-cell receptors (preferably CD4 or CD8) at the p56-lck binding site has been recognized for utility in the treatment of cancer, autoimmune disorders (e.g., SLE, multiple sclerosis, juvenile diabetes and rheumatoid arthritis), and infection with HIV and other viruses, for example as described in U.S. Pat. No. 5,250,431 with reference to certain modified T-cell CD4 and/or CD8 surface antigens.

Given the role of Lck in T cell activation and differentiation, it has been sought to identify and isolate gene(s) and protein(s) that associate with and modulate Lck, particularly the SH3 region of Lck. This has been accomplished in the present invention through the identification of LckBP1, including isolation of the murine LckBP1 gene, its incorporation as cDNA in a plasmid, and the expression of LckBP1 protein.

SUMMARY OF THE INVENTION

In one aspect the present invention entails substantially purified DNA encoding LckBP1, the DNA being substantially free of DNA that does not encode the amino acid sequence of LckBP1 or an LckBP1 analog.

Another aspect of the invention entails an expression vector for LckBP1 comprising the DNA of the invention operatively linked to at least one control sequence compatible with a suitable bacterial or eukaryotic host cell.

Still another aspect of the invention entails a bacterial host cell transformed, or a eukaryotic host cell transfected, with the expression vector of of the invention in a manner allowing the transformed host cell to express LckBP1 in a detectable quantity.

Yet another aspect of the invention entails a process for producing substantially purified LckBP1 by: culturing the bacterial host cell of the invention; using the cultured bacterial host cell to express LckBP1; and purifying the LckBP1 from the cultured bacterial host cell. Another aspect of the invention is the LckBP1 prepared by this process.

In another aspect the invention entails LckBP1 protein or a LckBP1 analog, substantially free of proteins other than LckBP1 protein or a LckBP1 analog, or an LckBP1 fragment or LckBP1 analog fragment analog substantially free of other proteins. Another aspect of the invention entails an antibody specifically binding the LckBP1 protein or LckBP1 analog of the invention.

Still another aspect of the invention entails a method of treating a tyrosine kinase modulated disorder in a mammal by administering the LckBP1 protein or LckBP1 analog of the invention, preferably in an amount sufficient to modulate lymphocyte activation.

In yet another aspect, the invention entails a diagnostic method for detecting tyrosine kinase-modulated disorder in a mammal by: isolating the Lck binding protein gene of the mammal to be diagnosed by immunologic assay using anti-LckBP1 protein or anti-LckBP1 fragment, or by hybridization to a PCR primer selected from SEQ ID NOS:1, 9–12 and 29; and determining the DNA sequence of the mammal's Lck binding protein gene, and comparing the DNA sequence of the mammal's Lck binding protein gene to the normal gene sequence; or determining the size of the mammal's Lck binding protein gene and comparing the gene size to the normal gene size.

Still another aspect of the invention entails a kit for the diagnosis of tyrosine kinase-modulated disorders, comprising: a series of PCR primers selected from SEQ ID NOS:40–64; or labelled or unlabelled LckBP1 protein or LckBP1 protein fragments as a competitive binding reagent.

Yet another asepct of the invention entails a transgenic animal, transfected to overespress LckBP1 or transfected to express no LckBP1.

BRIEF DESCRIPTION OF THE FIGURES

Figure 1B:
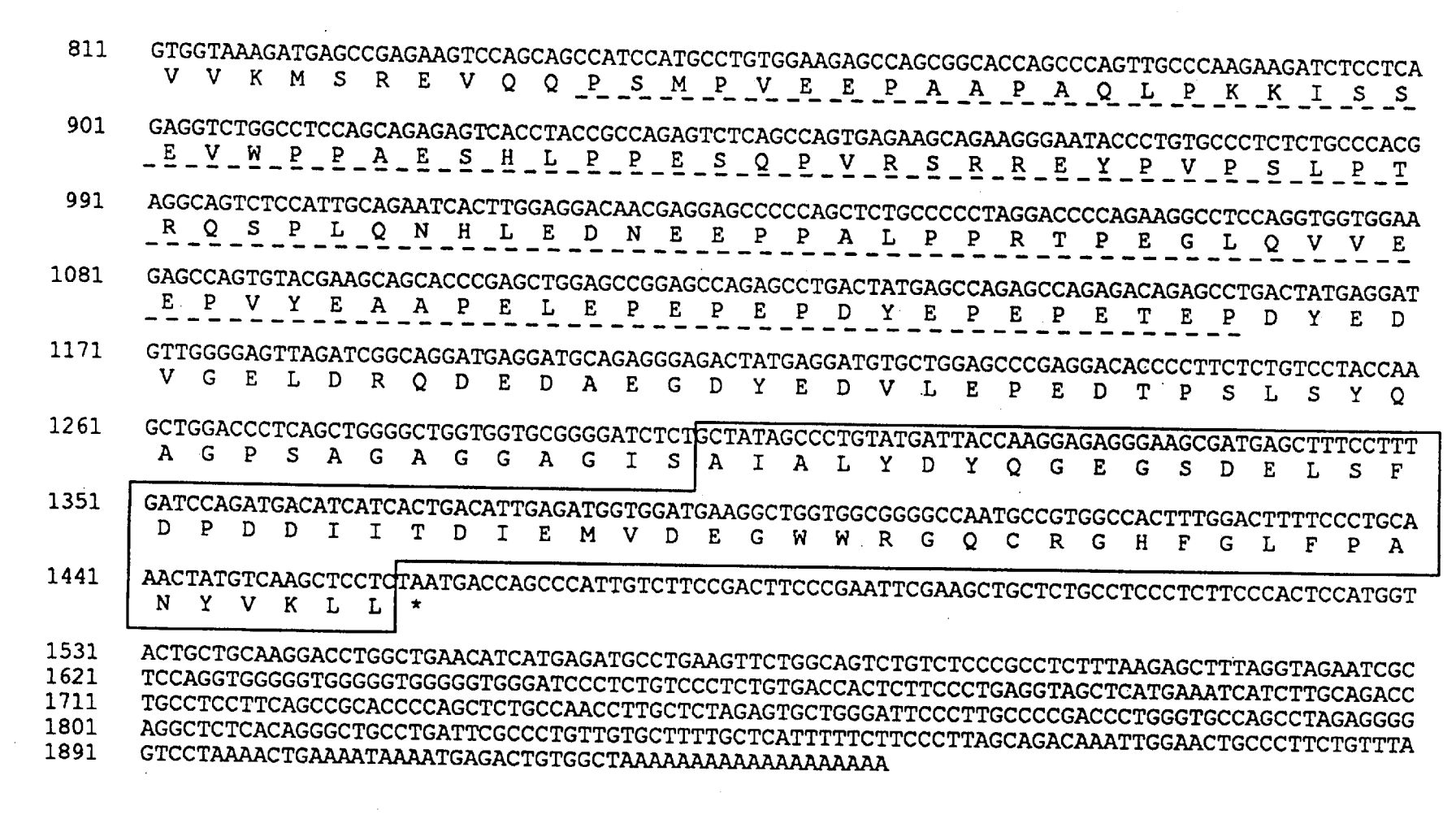

FIGS. 1A–B illustrates the single stranded nucleotide sequence in the sense direction (corresponding to SEQ ID NO:1) and the corresponding deduced amino acid sequence (corresponding to SEQ ID NO:2) of LckBP1. As described in greater detail below with reference to FIG. 1, the tandem 37-amino acid repeats are underlined, the proline-rich regions and proline-glutamate repeat are indicated by a dash under the corresponding one-letter amino acid codes, and the SH3 domain is boxed. Numerical positions of the nucleotides are shown on the left.

FIGS. 2A–B illustrates the homology of the deduced amino acid sequences of LckBP1 (corresponding to SEQ ID NO:2), of HS1 (corresponding to SEQ ID NO:3) and of P80/85 (corresponding to SEQ ID NO:4). The number of the starting amino acid of each line is listed in the column immediately to the left of the sequences. Within the sequences, a dash indicates that the HS1 or P80/85 amino acid is the same as that deduced for LckBP1; a dot indicates that no amino acid corresponding to the listed amino acid exists in the other species. As discussed in greater detail below, the brackets to the right of the sequences indicate the 37-amino acid repeat, the proline-rich and proline-glutamate repeat (E1A region). The SH3 domain is boxed.

FIG. 7 is a schematic representation of deletion mutants of the LckBP1 C-terminal region.

DETAILED DESCRIPTION OF THE INVENTION

Definitions

Figure 3:
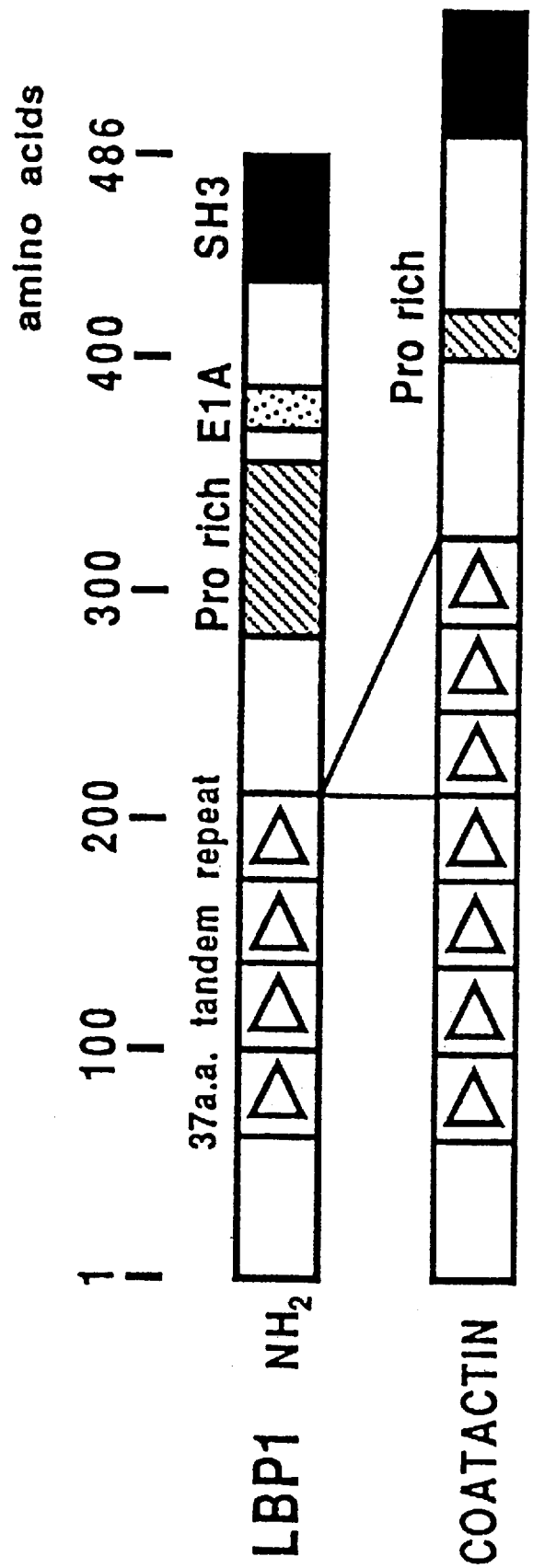
FIG. 3 is a schematic representation of the full LckBP1 structure, in which the arrowheads represent the four tandem 37-amino acid repeat motifs, the shaded box indicates the proline-rich region, the dotted box shows the E1A region containing the proline-glutamate repeat, and the filled box indicates the SH3 domain. The schematic correlation between LckBP1 and the functionally related tyrosine kinase substrate coatactin is also illustrated.

The following definitions are set forth to illustrate and define the meaning and scope of the various terms used to describe the invention herein.

The term "Lck" refers to the Lck tyrosine kinase molecule ($p56^{lck}$), a lymphocyte specific, non-receptor type src-family protein kinase of murine origin.

The term "LckBP1" refers to murine Lck binding protein.

The term "analog" or "analogous" DNA refers to other DNA sequences conservative, through the redundancy of the code, of the protein coded for by an identified DNA sequence.

The term "analog" or "analogous" protein or fragment refers to a protein or fragment having a conservative substitution, e.g., one or more Ser with Thr, Leu with Ser, Thr with Ile, and/or Thr with Ser, and/or having one or more amino acids in the murine (LckBP1) sequence replaced with the corresponding amino acid(s) (or deleting the LckBP1 amino acid where there is no corresponding amino acid or where substituting the corresponding amino acid would constitute a non-conservative change, such as between Leu and Pro) in the human (HS1) sequence.

The term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

The term "effective amount" means a dosage sufficient to provide treatment for the disease state being treated. This will vary depending on the patient, the disease and the treatment being effected.

Procedure Parameters

Unless specified to the contrary, standard techniques and parameters are used in the present invention. The procedures described herein employ aqueous media, solutions and buffers, and take place at atmospheric pressure within a temperature range from −70° C. to 100° C. (preferably from 10° C. to 35° C.; most preferably at "room" or "ambient" temperature, e.g., 20° C.). Further, unless otherwise specified, the reaction times and conditions are intended to be approximate, e.g., taking place at about atmospheric pressure within a temperature range of about −70° C. to about 100° C. (preferably from about 100° C. to about 35° C.; most preferably about 20° C.) over a period of about 1 to about 10 hours (preferably about 5 hours). Parameters given in the Examples are intended to be specific, not approximate.

Isolation and purification of the compounds and intermediates described herein can be effected, if desired, by any suitable separation or purification procedure such as, for example, filtration, extraction, column chromatography, thin-layer chromatography or thick-layer chromatography, electrophoresis, blotting (e.g., west-western) or a combination of these procedures. Specific illustrations of suitable separation and isolation procedures can be had by reference to the examples hereinbelow. However, other equivalent separation or isolation procedures can, of course, also be used.

The term "q.s." means adding a quantity sufficient to achieve a stated function, e.g., to bring a solution to the desired volume (i.e., 100%).

Identification, Characterization, Isolation and Expresion of LckBP1

The LckBP1 cDNA and protein, and the LckBP1 fragment cDNAs and proteins of the present invention are disclosed herein by sequence listing; the sequence listings for these cDNAs and proteins can be employed by those skilled in the art, using accepted methodology, in the complete practice of the invention as described. For example, see Sambrook, Fritsch and Maniatis, *Molecular Cloning: a laboratory manual*, Second Edition (Cold Spring Harbor Laboratory Press, New York) 1989.

Alternatively, those skilled in the art can practice the invention by repeating the experimental procedures carried out by the present inventors for the identification, characterization, isolation and expression of LckBP1. As described in greater detail in the Examples below, initially, a molecule (partial murine LckBP1) that associates with the SH3 domain of murine Lck was identified and isolated from a cDNA expression library. Confirmational testing demonstrated that the molecule so-isolated in fact binds to the SH3 domain of murine Lck. The cDNA corresponding to the partial murine LckBP1 was sequenced, which sequence was used to identify and sequence the full length cDNA for murine LckBP1. The full length cDNA was used to express and sequence murine LckBP1 protein. Active fragments of murine LckBP1 were identified. The amino acid sequence of the murine LckBP1 and structural features of the protein were characterized and compared to sequences and features of the published corresponding human and chicken proteins. Certain murine/human homologous regions were identified as active fragments of particular interest. Additional characterization included confirmation of in vivo association and expression in various cell lines.

Starting Materials
  Cells

The T cell lines KKF, NCKA, KgV, AKR1, originally derived from Gross virus-infected BALB/k thymocytes (Hashimoto, 1990 *J. Immunology*, 144, 1518–1525; Punt et al., 1991 *J. Exp. Med.*, 174, 775–783), and WEHI231 can be maintained in RPMI 1640 with 10% fetal calf serum. Murine NIH3T3 cells, and BALB/3T3 clone A31 can be maintained in modified Eagle's medium with 10% calf serum. Thymocytes can be prepared from 7-week-old mice.

Preparation of GST and GST-LckBP1 specific antibody

GST-specific antibody can be generated in a rabbit immunized with the GST protein, and used to detect GST. The LckBP1-specific antibody can be generated in a rabbit immunized with GST-LckBP1-#4 (amino acids 215–335 of LckBP1), and used to detect LckBP1.

Immuno-precipitation and Western blot analysis

Cell lysates ($5 \times 10^6$–$2 \times 10^7$ cells) can be prepared by lysis with TNE buffer (10 mM Tris-HCl, pH 7.8, 1% NP-40, 0.15M NaCl, 1 mM EDTA, 10 mg/ml aprotinin) and incubated with 10 ml of anti-LckBP1 antibody or 60 ml of anti-Lck antibody (Santa Cruz). Immune complexes can be recovered by the addition of 10 ml of protein A-Sepharose (Pharmacia), followed by rotation for 1 h at 4° C. The beads are washed 5 times with TNE buffer, lysed with SDS sample buffer, and the resulting solutions boiled for 10 min. Proteins can be separated by SDS-PAGE and transferred to nitrocellulose filters. The filters are blocked with TBST buffer (10 mM Tris-HCl, pH 8.0, 0.15M NaCl, 0.05% Tween 20) containing 5% skim milk and incubated with anti-LckBP1 antibody (1/400 dilution).

Nucleotide Sequence for LckBP1

Full length cDNA of the invention encoding for LckBP1 has 2,003 base pairs, with a 1,458 base pair open reading frame, as set forth in FIG. 1 (SEQ ID NO:1).

Amino Acid Sequence for LckBP1

LckBP1 is a 486 amino acid protein having a deduced molecular weight of 54-kDa, as set forth in FIGS. 1 and 2 (SEQ ID NO:2).

Characterization of LckBP1

As described in greater detail below, and illustrated with reference to FIGS. 1 to 4, the LckBP1 molecule has four structurally significant motifs, i.e.: four tandem 37-amino acid repeats (underlined in FIG. 1); a proline-rich region (identified by dashes under the amino acids in FIG. 1); a proline-glutamate repeat (also identified by dashes under the amino acids in FIG. 1); and a SH3 domain (boxed in FIGS. 1 and 2). An amino acid comparison, illustrating the sequence homology of LckBP1 with the human hematopoetic-specific protein (HS1) and the chicken src substrate p80/85, aligned using the Pileup command of UWGCG software, is shown in FIG. 2, where the structural motifs are identified in the right margin. The LckBP1 molecule is schmatically represented and compared to coatactin in FIG. 3. coatactin is another protein tyrosine kinase substrate (it is involved in a variety of tissues/organs/species in pTK signal transduction) the structure of which bears the illustrated similarities to LckBP1. This similarity in structure lends further support to the presently asserted significance and utilities of LckBP1.

Figure 4:
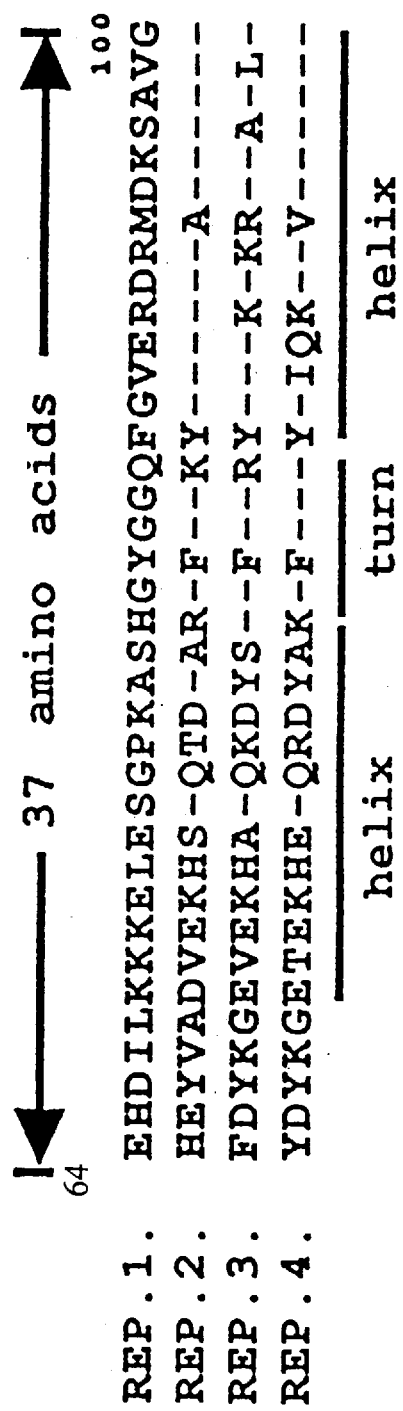
FIG. 4 illustrates the alignment of the four tandem 37-amino acid repeat motifs, starting with amino acid 64 of the complete sequence, including REP. 1 (corresponding to SEQ ID NO:5), REP. 2 (corresponding to SEQ ID NO:6), REP. 3 (corresponding to SEQ ID NO:7), and REP. 4 (corresponding to SEQ ID NO:8). The predicted helix-turn-helix motif of the repeat is indicated by underlining at the bottom of the aligned sequences.

The first motif is a four tandem 37-amino acid repeat at the N-terminal region (amino acids 64–211), the allignment of which is illustrated in FIG. 4. The protein sequence of these repeat motifs is very similar to those in human HS1 (see FIG. 2), which also contains four tandem 37-amino-acid repeat motifs in the N-terminal region (Kitamura et al., 1989 *Nucleic Acids Res.*, 17, 9367–9379). Chicken p80/85 has seven direct repeats (Wu et al., 1991 *Mol. Cell. Biol.*, 11, 5113–5124), as does murine coatactin. The repeat motif contains a predicted helix-turn-helix motif (underlined in FIG. 4) based on the Chou-Fasman and Garnier-Osguthorpe-Robson algorithm (Chou and Fasman, 1987 *Annu. Rev. Biochem.*, 47, 251–276; Garnier et al., 1978 *J. Mol. Biol.*, 120, 97–120). The helix-turn-helix structure is often found in the DNA binding domain of transcription factors (reviewed by Harrison and Aggarwal, 1991 *Annu. Rev. Biochem.*, 59, 933–969). As shown in FIG. 2, the HS1 motif is 94% identical with the four 37-amino acid tandem repeats of LckBP1. This is predictive of similar in vivo functionality for the two proteins, i.e., a role in DNA binding for the repeat motif in LckBP1. HS1 has been identified in both the cytoplasmic and the nuclear fraction (Kitamura et al., 1989; Yamanashi et al., 1993 *Proc. Natl. Acad. Sci. USA*, 90, 3631–3635).

Figure 5:
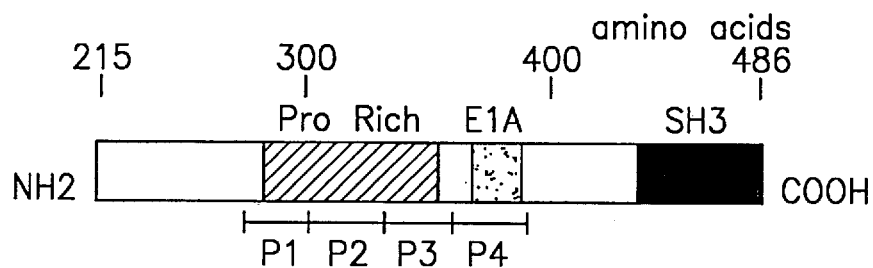
FIG. 5 is a schematic representation of the portion of the LckBP1 structure from amino acid 215 to amino acid 486, illustrating the location of four peptide fragments (P1 to P4) and the Lck SH3 domain binding site. The amino acid sequences of the four peptide fragments are illustrated below the schematic representation as follows: P1 (amino acids 274–301, corresponding to SEQ ID NO:9), P2 (amino acids 302–335, corresponding to SEQ ID NO:10) where the double underlining indicates conserved pralines among HS1 and coatactin, P3 (amino acids 336–360, corresponding to SEQ ID NO:11) where a potential MAP kinase phosphorylation site is boxed, and P4 (amino acids 354–390, corresponding to SEQ ID NO:12).

The second motif is a proline-rich region located at the C-terminal central region (amino acids 281–353). The proline-rich region is also conserved in HS1 and p80/85 (Kitamura et al., 1989; WU et al., 1991; FIG. 2). Proline-rich regions are typical of SH3 domain binding regions (Li et al., 1993; Rozakis-Adcock, 1993; Ren et al., 1993, 1994), the location of which in LckBP1 is illustrated in greater detail in FIG. 5A, where four fragments (P1 to P4) for analysis of the Lck SH3 domain binding site are shown (the double underlined section illustrates conserved prolines among HS1 and coactin). These proline rich regions are predictive of association of the proline-rich region in LckBP1 with the SH3 region in Lck. While association between the SH3 domain in the src kinase family and the proline-rich regions of other HS1/coatactin family member proteins has not been directly shown, chicken p80/85 is a known substrate of src tyrosine kinase (Wu et al., 1991), which correlates with the proline-rich region containing the conserved prolines being a src family SH3 binding region. A second proline-rich region contains a potential MAP serine/threonine kinase recognition site (the boxed portion of fragment P3 in FIG. 5A), and binds with the SH3 region in Lck. Lck controls MAP kinase activity in murine T cell lines (Ettehadieh et al., 1992 *Science*, 255, 853–855). MAP kinase modulation of the association of Lck and LckBP1 by modification of the potential kinase site in LckBP1 can be investigated by determining whether LckBP1 is a substrate of MAP kinase.

The third motif of LckBP1 is a proline-glutamate repeat (identified as E1A in FIGS. 4, 5 and 7A) located immediately to the C-terminal side of the proline-rich region (amino acids 368–386). This proline-glutamate repeat is conserved in HS1 but not in p90/85 (FIG. 2). HS1 was originally identified from a human B cell cDNA library using a 13S Ad2E1A DNA probe. It is reported that the proline-glutamate repeat was the homologous region between the HS1 and E1A genes (Kitamura et al., 1989), which predicts the functional importance of this proline-glutamate repeat.

The fourth motif in the LckSP1 C-terminal region is a typical SH3 structure (amino acids 434–486), which has been identified in three categories of proteins: 1) cytoskeleton-associated proteins, such as chicken p85 (Wu et al., 1991), myosin heavy chain (Drubin et al., 1990), yeast actin-binding protein 1 (Drubin et al., 1990), fodrin (McMahon et al., 1987), and a-spectrin (McMahon et al., 1987); 2) non-receptor type tyrosine kinases (Pawson, 1988); and 3) adapter molecules such as Grb2 (Lowenstein et al., 1992), Sem-5 (Clark et al., 1992), and Drk (Simon et al., 1993; Olivier et al., 1993). As illustrated in FIG. 2, the SH3 domain in LckBP1 shows much greater amino acid sequence homology with HS1 (92%) and p90/85 (73%) than with Grb2-SH3 (32% at SH3-N-terminal; 32% SH3-C-terminal), Lck (27%) or c-src (29%), which is predictive that the SH3 domain in LckBP1, like p80/85, associates with the cytoskeleton. Additionally, LckBP1 has no actin-binding sites, predictive of its function as an adapter protein. The association of the SH3 domain with proline-rich sequences (Li et al., 1993; Ren et al., 1993, 1994; Rozakis-Adcock, 1993), and the presence of the SH3 domain in LckBP1 is consistent with a role for LckBP1 as an adapter molecule of Lck or cytoskeleton-associating protein through its SH3 domain association with various proline-rich molecules. Additionally, the LckBP1 SH3 domain can bind to proline-rich regions of LckBP1 itself, thereby regulating its own function.

Besides these major domains, potential tyrosine phosphorylation sites (E/DY) are found in the 37-amino acid direct repeat motif (amino acids 102–103, 139–140, 152–153, 176–177, 189–190), in the proline-rich region (amino acids 322–323), in the proline-glutamate repeat (amino acids 377–378, 387–388), in the region between the proline-glutamate repeat and the SH3 domain (amino acids 404–405), and in the SH3 domain (amino acids 439–440). A myosin heavy-chain kinase phosphorylation site (KXXS; Breska et al., 1989; Kemp and Rearson, 1991) is also seen in the 37-amino acid repeat motif (amino acids 109–112, 146–149, 183–186). A potential MAP kinase site (P-P/R/K-S/T-P; Alvarez et al., 1991; Gonzalez et al., 1991) is observed in proline-rich region (amino acids 350–353). is The sequence homology search (best fit command; UWGCG software) showed that murine LckBP1 has 86% homology to human HS1 and 50% to chicken p80/85 at the amino acid level. The four major domains delineated in LckBP1 were also found in HS1.

Active Fragments of LckBP1

Based on the foregoing characterization and sequence homology analyses, plus the data reported below in the Examples, the complete LckBP1 protein and fragments are particularly useful as compositions and in the methods of the invention. Similarly useful (prepared by recombinant methodology known to those skilled in the art) are the analogous proteins and fragments substituting, e.g., one or more Ser with Thr, Leu with Ser, Thr with Ile, and/or Thr with Ser, and/or replacing the one or more amino acids in the murine (LckBP1) sequence with the corresponding amino acid(s) (or deleting the LckBP1 amino acid where there is no corresponding amino acid or where substituting the corresponding amino acid would constitute a non-conservative change, such as between Leu and Pro) in the human (HS1) sequence, such as:

| P1 | Met | Ser | Arg | Glu | Val | Gln | Gln | Pro | Ser | Met | Pro | Val | Glu | Glu | Pro | Ala |
|----|-----|-----|-----|-----|-----|-----|-----|-----|-----|-----|-----|-----|-----|-----|-----|-----|
|    | Ala | Pro | Ala | Gln | Leu | Pro | Lys | Lys | Ile | Ser | Ser | Glu |     |     |     |     |
|    | (SEQ ID NO:9) | | | | | | | | | | | | | | | |
| P2 | Val | Trp | Pro | Pro | Ala | Glu | Ser | His | Leu | Pro | Pro | Glu | Ser | Gln | Pro | Val |
|    | Arg | Ser | Arg | Arg | Glu | Tyr | Pro | Val | Pro | Ser | Leu | Pro | Thr | Arg | Gln | Ser |
|    | Pro | Leu | | | | | | | | | | | | | | |
|    | (SEQ ID NO:10) | | | | | | | | | | | | | | | |
| P3 | Gln | Asn | His | Leu | Glu | Asp | Asn | Glu | Glu | Pro | Pro | Ala | Leu | Pro | Pro | Arg |
|    | Thr | Pro | Glu | Gly | Leu | Gln | Val | Val | Glu | | | | | | | |
|    | (SEQ ID NO:11) | | | | | | | | | | | | | | | |
| P4 | Glu | Gly | Leu | Gln | Val | Val | Glu | Glu | Pro | Val | Tyr | Glu | Ala | Ala | Pro | Glu |
|    | Leu | Glu | Pro | Glu | Pro | Glu | Pro | Asp | Tyr | Glu | Pro | Glu | Pro | Glu | Thr | Glu |
|    | Pro | Asp | Tyr | Glu | | | | | | | | | | | | |
|    | (SEQ ID NO:12) | | | | | | | | | | | | | | | |

-continued

| Name | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| P2A | Val | Trp | Pro | Pro | Ala | Glu | Ser | His | Leu | Pro | Pro | Glu | Ser | Gln | Pro | Val |
|  | Arg | Thr | Arg | Arg | Glu | Tyr | Pro | Val | Pro | Ser | Leu | Pro | Thr | Arg | Gln | Ser |
|  | Pro | Leu |  |  |  |  |  |  |  |  |  |  |  |  |  |  |
| (SEQ ID NO:13) | | | | | | | | | | | | | | | | |
| P2B | Val | Trp | Pro | Pro | Ala | Glu | Ser | His | Leu | Pro | Pro | Glu | Ser | Gln | Pro | Val |
|  | Arg | Ser | Arg | Arg | Glu | Tyr | Pro | Val | Pro | Leu | Leu | Pro | Thr | Arg | Gln | Ser |
|  | Pro | Leu |  |  |  |  |  |  |  |  |  |  |  |  |  |  |
| (SEQ ID NO:14) | | | | | | | | | | | | | | | | |
| P2C | Val | Trp | Pro | Pro | Ala | Glu | Ser | His | Leu | Pro | Pro | Glu | Ser | Gln | Pro | Val |
|  | Arg | Ser | Arg | Arg | Glu | Tyr | Pro | Val | Pro | Ser | Leu | Pro | Ile | Arg | Gln | Ser |
|  | Pro | Leu |  |  |  |  |  |  |  |  |  |  |  |  |  |  |
| (SEQ ID NO:15) | | | | | | | | | | | | | | | | |
| P2D | Val | Trp | Pro | Pro | Ala | Glu | Ser | His | Leu | Pro | Pro | Glu | Ser | Gln | Pro | Val |
|  | Arg | Ser | Arg | Arg | Glu | Tyr | Pro | Val | Pro | Ser | Leu | Pro | Thr | Arg | Gln | Thr |
|  | Pro | Leu |  |  |  |  |  |  |  |  |  |  |  |  |  |  |
| (SEQ ID NO:16) | | | | | | | | | | | | | | | | |
| P2E | Val | Trp | Pro | Pro | Ala | Glu | Ser | His | Leu | Pro | Pro | Glu | Ser | Gln | Pro | Val |
|  | Arg | Ser | Arg | Arg | Glu | Tyr | Pro | Val | Pro | Ser | Leu | Pro | Thr | Arg | Gln | Ser |
| (SEQ ID NO:17) | | | | | | | | | | | | | | | | |
| P2F | Val | Trp | Pro | Pro | Ala | Glu | Ser | His | Leu | Pro | Pro | Glu | Ser | Gln | Pro | Val |
|  | Arg | Thr | Arg | Arg | Glu | Tyr | Pro | Val | Pro | Leu | Leu | Pro | Ile | Arg | Gln | Thr |
|  | Pro | Leu |  |  |  |  |  |  |  |  |  |  |  |  |  |  |
| (SEQ ID NO:18) | | | | | | | | | | | | | | | | |
| P2G | Val | Trp | Pro | Pro | Ala | Glu | Ser | His | Leu | Pro | Pro | Glu | Ser | Gln | Pro | Val |
|  | Arg | Ser | Arg | Arg | Glu | Tyr | Pro | Val | Pro | Leu | Leu | Pro | Thr | Arg | Gln | Thr |
|  | Pro | Leu |  |  |  |  |  |  |  |  |  |  |  |  |  |  |
| (SEQ ID NO:19) | | | | | | | | | | | | | | | | |
| P2H | Val | Trp | Pro | Pro | Ala | Glu | Ser | His |  | Pro | Pro | Glu | Ser | Gln | Pro | Val |
|  | Arg | Ser | Arg | Arg | Glu | Tyr | Pro | Val | Pro | Leu | Leu | Pro | Ile | Arg | Gln | Ser |
|  | Leu |  |  |  |  |  |  |  |  |  |  |  |  |  |  |  |
| (SEQ ID NO:20) | | | | | | | | | | | | | | | | |
| P2I | Val | Trp | Pro | Pro | Val | Gly | Thr | Pro | Pro | Ser | Ser | Glu | Ser | Gln | Pro | Val |
|  | Arg | Ser | Arg | Arg | Glu | Tyr | Pro | Val | Pro | Ser | Leu | Pro | Thr | Arg | Gln | Ser |
|  | Pro | Leu |  |  |  |  |  |  |  |  |  |  |  |  |  |  |
| (SEQ ID NO:21) | | | | | | | | | | | | | | | | |
| P3A | Gln | Asn | His |  | Glu | Asp | Asn | Glu | Glu | Pro | Pro | Ala | Leu | Pro | Pro | Arg |
|  | Thr | Pro | Glu | Gly | Leu | Gln | Val | Val | Glu |  |  |  |  |  |  |  |
| (SEQ ID NO:22) | | | | | | | | | | | | | | | | |
| P3B | Gln | Asn | His | Leu | Glu | Asp | Asn | Glu | Glu | Pro | Pro | Ala | Leu | Pro | Pro | Arg |
|  | Thr |  | Glu | Gly | Leu | Gln | Val | Val | Glu |  |  |  |  |  |  |  |
| (SEQ ID NO:23) | | | | | | | | | | | | | | | | |
| P3C | Gln | Asn | His |  | Glu | Asp | Asn | Glu | Glu | Pro | Pro | Ala | Leu | Pro | Pro | Arg |
|  | Thr |  | Glu | Gly | Leu | Gln | Val | Val | Glu |  |  |  |  |  |  |  |
| (SEQ ID NO:24) | | | | | | | | | | | | | | | | |
| P3D | Gln | Asn | His | Leu | Glu | Asp | Asn | Glu | Glu | Pro | Pro | Ala | Leu | Pro | Pro | Arg |
|  | Ser | Pro | Glu | Gly | Leu | Gln | Val | Val | Glu |  |  |  |  |  |  |  |
| (SEQ ID NO:25) | | | | | | | | | | | | | | | | |
| P3E | Gln | Asn | His | Leu | Glu | Asp | Asn | Glu | Glu | Pro | Pro | Ala | Ser | Pro | Pro | Arg |
|  | Thr | Pro | Glu | Gly | Leu | Gln | Val | Val | Glu |  |  |  |  |  |  |  |
| (SEQ ID NO:26) | | | | | | | | | | | | | | | | |
| P3F |  |  | His | Leu | Glu | Asp | Asn | Glu | Glu | Pro | Pro | Ala | Leu | Pro | Pro | Arg |
|  | Thr | Pro | Glu | Gly | Leu | Gln | Val | Val | Glu |  |  |  |  |  |  |  |
| (SEQ ID NO:27) | | | | | | | | | | | | | | | | |
| P3G |  |  | His |  | Glu | Asp | Asn | Glu | Glu | Pro | Pro | Ala | Leu | Pro | Pro | Arg |
|  | Thr |  | Glu | Gly | Ser | Gln | Val | Val | Glu |  |  |  |  |  |  |  |
| (SEQ ID NO:28) | | | | | | | | | | | | | | | | |
| SH3 | Ala | Ile | Ala | Leu | Tyr | Asp | Tyr | Gln | Gly | Glu | Gly | Ser | Asp | Glu | Leu | Ser |
|  | Phe | Asp | Pro | Asp | Asp | Ile | Ile | Thr | Asp | Ile | Glu | Met | Val | Asp | Glu | Gly |
|  | Trp | Trp | Arg | Gly | Gln | Cys | Arg | Gly | His | Phe | Gly | Leu | Phe | Pro | Ala | Asn |
|  | Tyr | Val | Lys | Leu | Leu |  |  |  |  |  |  |  |  |  |  |  |
| (SEQ ID NO:29) | | | | | | | | | | | | | | | | |
| SH3A | Ala | Val | Ala | Leu | Tyr | Asp | Tyr | Gln | Gly | Glu | Gly | Ser | Asp | Glu | Leu | Ser |
|  | Phe | Asp | Pro | Asp | Asp | Ile | Ile | Thr | Asp | Ile | Glu | Met | Val | Asp | Glu | Gly |
|  | Trp | Trp | Arg | Gly | Gln | Cys | Arg | Gly | His | Phe | Gly | Leu | Phe | Pro | Ala | Asn |
|  | Tyr | Val | Lys | Leu | Leu |  |  |  |  |  |  |  |  |  |  |  |
| (SEQ ID NO:30) | | | | | | | | | | | | | | | | |
| SH3B | Ala | Ile | Ala | Ser | Tyr | Asp | Tyr | Gln | Gly | Glu | Gly | Ser | Asp | Glu | Leu | Ser |
|  | Phe | Asp | Pro | Asp | Asp | Ile | Ile | Thr | Asp | Ile | Glu | Met | Val | Asp | Glu | Gly |
|  | Trp | Trp | Arg | Gly | Gln | Cys | Arg | Gly | His | Phe | Gly | Leu | Phe | Pro | Ala | Asn |
|  | Tyr | Val | Lys | Leu | Leu |  |  |  |  |  |  |  |  |  |  |  |
| (SEQ ID NO:31) | | | | | | | | | | | | | | | | |
| SH3C | Ala | Ile | Ala | Leu | Tyr | Asp | Tyr | Gln | Gly | Glu | Gly | Ser | Asp | Glu | Leu | Ser |
|  | Phe | Asp | Pro | Asp | Asp | Ile | Ile | Ile | Asp | Ile | Glu | Met | Val | Asp | Glu | Gly |
|  | Trp | Trp | Arg | Gly | Gln | Cys | Arg | Gly | His | Phe | Gly | Leu | Phe | Pro | Ala | Asn |
|  | Tyr | Val | Lys | Leu | Leu |  |  |  |  |  |  |  |  |  |  |  |
| (SEQ ID NO:32) | | | | | | | | | | | | | | | | |

-continued

| | | | | | | | | | | | | | | | | |
|---|---|---|---|---|---|---|---|---|---|---|---|---|---|---|---|---|
| SH3D | Ala | Ile | Ala | Leu | Tyr | Asp | Tyr | Gln | Gly | Glu | Gly | Ser | Asp | Glu | Leu | Ser |
| | Phe | Asp | Pro | Asp | Asp | <u>Val</u> | Ile | Thr | Asp | Ile | Glu | Met | Val | Asp | Glu | Gly |
| | Trp | Trp | Arg | Gly | Gln | Cys | Arg | Gly | His | Phe | Gly | Leu | Phe | Pro | Ala | Asn |
| | Tyr | Val | Lys | Leu | Leu | | | | | | | | | | | |
| | (SEQ ID NO:33) | | | | | | | | | | | | | | | |
| SH3E | Ala | Ile | Ala | Leu | Tyr | Asp | Tyr | Gln | Gly | Glu | Gly | <u>Thr</u> | Asp | Glu | Leu | Ser |
| | Phe | Asp | Pro | Asp | Asp | Ile | Ile | Thr | Asp | Ile | Glu | Met | Val | Asp | Glu | Gly |
| | Trp | Trp | Arg | Gly | Gln | Cys | Arg | Gly | His | Phe | Gly | Leu | Phe | Pro | Ala | Asn |
| | Tyr | Val | Lys | Leu | Leu | | | | | | | | | | | |
| | (SEQ ID NO:34) | | | | | | | | | | | | | | | |
| SH3F | Ala | Ile | Ala | Leu | Tyr | Asp | Tyr | Gln | Gly | Glu | Gly | Ser | Asp | Glu | Leu | Ser |
| | Phe | Asp | Pro | Asp | Asp | Ile | Ile | Thr | Asp | Ile | Glu | Met | Val | Asp | Glu | Gly |
| | Trp | Trp | Arg | Gly | <u>Arg</u> | Cys | <u>His</u> | Gly | His | Phe | Gly | Leu | Phe | Pro | Ala | Asn |
| | Tyr | Val | Lys | Leu | Leu | | | | | | | | | | | |
| | (SEQ ID NO:35) | | | | | | | | | | | | | | | |
| SH3G | Ala | Ile | Ala | Leu | Tyr | Asp | Tyr | Gln | Gly | Glu | Gly | Ser | Asp | Glu | Leu | Ser |
| | Phe | Asp | Pro | Asp | Asp | Ile | Ile | Thr | Asp | Ile | Glu | Met | Val | Asp | Glu | Gly |
| | Trp | Trp | Arg | Gly | Gln | Cys | Arg | Gly | His | Phe | Gly | Leu | Phe | Pro | Ala | Asn |
| | Tyr | Val | Lys | Leu | Leu | <u>Glu</u> | | | | | | | | | | |
| | (SEQ ID NO:36) | | | | | | | | | | | | | | | |
| SH3H | Ala | Ile | Ala | Leu | Tyr | Asp | Tyr | Gln | <u>Ala</u> | <u>Ala</u> | Gly | Ser | Asp | Glu | Leu | Ser |
| | Phe | Asp | Pro | Asp | Asp | Ile | Ile | Thr | Asp | Ile | Glu | Met | Val | Asp | Glu | Gly |
| | Trp | Trp | Arg | Gly | Gln | Cys | Arg | Gly | His | Phe | Gly | Leu | Phe | Pro | Ala | Asn |
| | Tyr | Val | Lys | Leu | Leu | | | | | | | | | | | |
| | (SEQ ID NO:37) | | | | | | | | | | | | | | | |
| SH3I | Ala | Val | Ala | Leu | Tyr | Asp | Tyr | Gln | Gly | Glu | Gly | Ser | Asp | Glu | Leu | Ser |
| | Phe | Asp | Pro | Asp | Asp | <u>Val</u> | Ile | Thr | Asp | Ile | Glu | Met | Val | Asp | Glu | Gly |
| | Trp | Trp | Arg | Gly | Gln | Cys | Arg | Gly | His | Phe | Gly | Leu | Phe | Pro | Ala | Asn |
| | Tyr | Val | Lys | Leu | Leu | <u>Glu</u> | | | | | | | | | | |
| | (SEQ ID NO:38) | | | | | | | | | | | | | | | |
| SH3J | Ala | Ile | Ala | Leu | Tyr | Asp | Tyr | Gln | Gly | Glu | Gly | <u>Thr</u> | Asp | Glu | Leu | Thr |
| | Phe | Asp | Pro | Asp | Asp | Ile | <u>Thr</u> | <u>Ile</u> | Asp | Ile | Glu | Met | Val | Asp | Glu | <u>Gly</u> |
| | Trp | Trp | Arg | Gly | Gln | Cys | Arg | Gly | His | Phe | Gly | Leu | Phe | Pro | Ala | Asn |
| | Tyr | Val | Lys | Leu | Leu | | | | | | | | | | | |
| | (SEQ ID NO:39) | | | | | | | | | | | | | | | |

LckBP1 Association in vivo

The predicted molecular mass of LckBP1 is 54-kDa according to the deduced amino acid sequence of the LckBP1 cDNA. LckBP1 of the invention migrates at 85-kDa in SDS-PAGE. Similarly, HS1 migrates at 75-kDa in SDS-PAGE, whereas its predicted molecular mass is 54-kDa (Kitamura et al., 1989), and chicken coatactin appears at 80 and 85-kDa on SDS-PAGE, while its predicted size is 63-kDa (Wu et al., 1991). Such differences between predicted molecular size and that estimated by SDS-PAGE are attributable to phosphorylation, glycosylation or protein folding effects on molecular size as determined by SDS-PAGE. Similar discrepancies between predicted and SDS-PAGE-estimated size have been observed in other HS1/coatactin family members besides HS1, indicating common mechanisms for modification or protein folding.

In immuno-precipitation experiments, anti-LckBP1 antibody recognized an 85-kDa (p85) protein molecule in thymocytes, and two major proteins, 80-kDa (p80) and p85, in the KKF and 2B4 cell lines. Anti-Lck antibody selectively precipitated p85 from adult thymocyte, KKF, and 2B4 cell lysates, indicating that p85 is an association molecule of Lck in vivo. However, p80 which is present in KKF and 2B4 cells was not detected by anti-Lck antibody. Western blot analysis with anti-LckBP1 antibody to verify the expression of p80 and p85 in various cell lines, revealed p85 only in a hematopoietic lineage cells, and not in fibroblast cell lines, whereas p80 was identified in both hematopoietic and some fibroblast cell lines. Thus, antiserum generated against the recombinant LckBP1 molecule detected two major size of proteins, but only one, p85, was detected in thymocytes by SDS-PAGE analysis using this antiserum. Accordingly, it is predicted that LckBP1-p85, but not p80, associates with Lck in vivo. Since LckBP1 can associate with Lck in vitro, it is likely that the anti-LckBP1 antiserum detects LckBP1 as a p85 species on SDS-PAGE. Currently, it is not known whether p80 and p85 are encoded by the same gene. However Wu et al. (1991) showed that there are two forms of proteins p80/85 in chicken Src substrate, and based on biochemical evidence, suggested that p80 may be an alternative form of p85. Thus, the p80 identified in our experiments might be also encoded by the LckBP1 gene and modified differently from p85 by mechanisms such as proteolytic processing or alternative splicing. Possibly, the different modification prevents p80 from associating with Lck. Finally, p80 might represent a distinct but closely related protein to LckBP1.

The SH3 region in Lck binds to the multiple proline-rich regions of LckBP1. This is consistent with recent reports of the protein association between SH3 segments and proline-rich fragments. Recently, Yamanashi et al. (1993) reported the association of HS1 with the Lyn tyrosine kinase in B cells, and rapid tyrosine phosphorylation after stimulation with antibody to IgM. Analysis of the binding region showed that HS1 associates with the SH2 domain of Lyn (Yamanashi, et al., 1993), indicating similar binding between LckBP1 and the SH2 region of Lck, given the relationship between LckBP1 and HS1, and since Lyn and Lck belong to the same Src family. We detected LckBP1/p85 only in hematopoietic lineage cells. Similarly, HS1 expression is restricted to hematopoietic lineage cells. Furthermore, both proteins associate with Src tyrosine protein kinases. Such evidence indicates that these molecules play an essential role in development or activation of hematopoietic lineage cells, irrespective of whether these products are human and murine counterparts or only closely related.

Expression Pattern of LckBP1

The LckBP1 protein is expressed not only in the pre-T cell line KKF, but also in the mature T cell line 2B4. To analyze the expression pattern of LckBP1 in various cell lines, we performed Western blot analysis using cell lysates separated by SDS-PAGE, transferred to nitrocellulose filters, and probed with anti-LckBP1 antibody or anti-GST antibody.

Expression of p85 was observed in the murine transformed T cell lines NCKA (TCR⁻), KgV (TCRαβ⁺), and ARK1 (TCRαβ⁺). In addition, p85 expression was detected in the B cell lymphoma WEHI231, but not in NIH3T3 cells or BALB/3T3 clone A31, whereas p80 was expressed in all cell lines examined. These results indicate that LckBP1-p85 is expressed in a hematopoietic-specific manner, while p80 is expressed ubiquitously. The filter probed with anti-GST antibody showed some background proteins, probably is representing non-specific binding. This expression pattern data further confirm the significance of LckBP1-p85 and the likely insignificance of LckBP1-80.

Pharmaceutical Utility, Testing and Administration

General Utility

LckBP1, the SH3 region and the fragments ABC corresponding to human are useful for treating tyrosine kinase modulated disorders, particularly including immune disorders such as allergy, autoimmune diseases, allograft and xenograft rejection and cancer in a mammal, by administering to a mammal in need of such treatment LckBP1 or a peptide selected from the murine/human overlapping regions in an amount sufficient to up-regulate lymphocyte activation.

Testing

In vitro and in vivo binding of a protein to a target receptor is determined, for example, as described by Cicchetti et al. (1992 *Science*, 257, 803–806), such as the modification described in Examples 6 and 16, below.

General immunosuppressive activity is associated with the inhibition of Inosine 5'-Monophosphate Dehydrogenase ("IMPDH"), which is also associated with anti-inflammatory, anti-viral, anti-tumor, and/or anti-psoriatic activity. In vitro assays measuring the inhibition of IMPDH, for example, by determining the level of NADH formation according to the method of Anderson, J. H. and Sartorelli, A. C., *J. Biol. Chem.*, 243:4762–4768 (1968) are predictive of such activity.

Autoimmune activity is determined, e.g., utilizing experimental allergic encephalomyelitis, by a modification of a procedure initially described by Grieg, et. al., *J. Pharmacol. Exp. Ther.*, 173:85 (1970).

Activity to prevent the rejection of organ or tissue allografts in experimental animals is determined, for example, as described by Hao, et al., *J. Immunol.*, 139:4022–4026 (1987). In addition, U.S. Pat. No. 4,707,443 and EP 226062, incorporated herein by reference, also describe assays for activity in prevention of allograft rejection by detection of IL-2R levels. Human clinical trials to establish efficacy in preventing rejection of solid organ transplants (such as renal) are conducted, e.g., as described by Lindholm, Albrechtsen, Tufveson, et al., "A randomized trial of cyclosporin and prednisolone versus cyclosporin, azathioprine and prednisolone in primary cadaveric renal transplantation," *Transplantation*, 54:624–631 (1992). Human clinical trials for graft vs. host disease are conducted, e.g., as described by Storb, Deeg, Whitehead, et al., "Methotrexate and cyclosporin compared with cyclosporin alone for prophylaxis of acute graft versus host disease after marrow transplantation for leukemia." *New England J. Med.*, 314:729–735 (1986).

Immunosuppressive activity is determined by both in vivo and in vitro procedures. In vivo activity is determined, e.g., utilizing a modification of the Jerne hemolytic plaque assay, (Jerne, et al., "The agar plaque technique for recognizing antibody producing cells," *Cell-bound Antibodies*, Amos, B. and Kaprowski, H. editors (Wistar Institute Press, Philadelphia) 1963, p. 1091. In vitro activity is determined, e.g., by an adaptation of the procedure described by Greaves, et al., "Activation of human T and B lymphocytes by polyclonal mitogens," *Nature*, 248:698–701 (1974).

Administration

The LckBP1 and active fragments, including the SH3 region and the analogous proteins and fragments substituting, e.g., one or more Ser with Thr, Leu with Ser, Thr with Ile, and/or Thr with Ser, and/or replacing the one or more amino acids in the murine (LckBP1) sequence with the corresponding amino acid(s) (or deleting the LckBP1 amino acid where there is no corresponding amino acid or where substituting the corresponding amino acid would constitute a non-conservative change, such as between Leu and Pro) in the human (HS1) sequence (e.g., SEQ ID NOS:2, 10, 11, and 13–39) are administered at a therapeutically effective dosage, e.g., a dosage sufficient to provide treatment for the disease states previously described. Administration of the active agents of the invention or the pharmaceutically acceptable salts thereof can be via any of the accepted modes of administration for agents that serve similar utilities.

While human dosage levels have yet to be optimized for the protein and fragments of the invention, generally, a daily dose is from about 0.001 to 100.0 µg/kg of body weight, depending in part upon the size of the active agent, as will be apparent to those skilled in the art. For the protein, a presently preferred dosage level is about 0.01 to 30 µg/kg of body weight, most preferably about 0.1 to 20 µg/kg of body weight. For the active fragments a presently preferred dosage level is about 0.04 to about 2.0 µg/kg of body weight. Thus, for administration to a 70 kg person, the dosage range would be about 0.07 µg to 2.1 mg per day, preferably about 7.0 µg to 1.4 mg per day for the protein, and preferably about 2.8 to 140.0 µg per day for the active fragments. The amount of active agent administered will, of course, be dependent on the subject and disease state being treated, the severity of the affliction, the manner and schedule of administration and the judgment of the prescribing physician. In mammals other than man, such as horses, dogs and cattle, higher doses may be required.

In employing the proteins of this invention for treatment of the above conditions, any pharmaceutically acceptable mode of administration can be used. The proteins can be administered either alone or in combination with other pharmaceutically acceptable excipients, including solid, semi-solid, liquid or aerosol dosage forms, such as, for example, tablets, capsules, powders, liquids, suspensions, suppositories, aerosols or the like. The proteins can also be administered in sustained or controlled release dosage forms, including depot injections, osmotic pumps, pills, transdermal (including electrotransport) patches, and the like, for the prolonged administration of the active agent at a predetermined rate, preferably in unit dosage forms suitable for single administration of precise dosages. The compositions will typically include a conventional pharmaceutical carrier or excipient and a protein or active fragment of the invention. In addition, these compositions may include other medicinal agents, pharmaceutical agents, carriers, adjuvants, etc.

Pharmaceutically acceptable salts retain the desired biological activity of the protein or active fragment without toxic side effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalene disulfonic acids, polygalacturonic acid and the like; (b) base addition salts formed with polyvalent metal cations such as zinc, calcium, bismuth, barium, magnesium, aluminum, copper, cobalt, nickel, cadmium, and the like; or with an organic cation formed from N,N'-dibenzylethylenediamine or ethylenediamine; or (c) combinations of (a) and (b), e.g., a zinc tannate salt and the like. Such salts are also intented as the active agents of the present invention.

Generally, depending on the intended mode of administration, the pharmaceutically acceptable composition will contain about 0.01% to about 90%, preferably about 0.5% to 50%, by weight of a protein or active fragment of the invention, the remainder being suitable pharmaceutical excipients, carriers, etc.

One preferred manner of administration for the conditions detailed above is oral, using a convenient daily dosage regimen which can be adjusted according to the degree of affliction. As those skilled in the art will appreciate, each protein has its own characteristics that lead to a particular solution for such oral administration. Typically, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active agent as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc. Actual methods of preparing such dosage forms are known, or will be apparent, to those skilled in this art; for example, see Remington's Pharmaceutical Sciences, Mack Publishing Company, Easton, Pennsylvania, 15th Edition, 1975. The composition or formulation to be administered will, in any event, contain a quantity of the active agent in an amount effective to alleviate the symptoms of the subject being treated.

Dosage forms or compositions containing active agent in the range of 0.005% to 95% with the balance made up from non-toxic carrier may be prepared.

For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained release formulations and the like. Such compositions may contain 0.01%–95% active ingredient, preferably 0.01–50%.

For a solid dosage form, the solution or suspension, in for example propylene carbonate, vegetable oils or triglycerides, is preferably encapsulated in a gelatin capsule. Such diester solutions, and the preparation and encapsulation thereof, are disclosed in U.S. Pat. Nos. 4,328,245; 4,409,239; and 4,410,545. For a liquid dosage form, the solution, e.g. in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active agent in vegetable oils, glycols, triglycerides, propylene glycol esters (e.g. propylene carbonate) and the like, and encapsulating these solutions or suspensions in hard or soft gelatin capsule shells.

Other useful formulations include those set forth in U.S. Pat. Nos. Re. 28,819 and 4,358,603.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

A more recently devised approach for parenteral administration employs the implantation of a slow-release or sustained-release system, such that a constant level of dosage is maintained. See, e.g., U.S. Pat. No. 3,710,795.

The percentage of active agent contained in such parenteral compositions is highly dependent on the specific nature thereof, as well as the activity of the active agent and the needs of the subject. However, percentages of active agent of 0.01% to 10% in solution are employable, and will be higher if the composition is a solid which will be subsequently diluted to the above percentages.

Delivery of the protein or active fragments of the present invention to the subject over prolonged periods of time, for example, for periods of one week to one year, may be accomplished by a single administration of a controlled release system containing sufficient active agent for the desired release period. Various controlled release systems, such as monolithic or reservoir-type microcapsules, depot implants, osmotic pumps, vesicles, micelles, liposomes, transdermal patches, iontophoretic devices and alternative injectable dosage forms may be utilized for this purpose. Localization at the site to which delivery of the active agent is desired is an additional feature of some controlled release devices, which may prove beneficial in the treatment of certain disorders.

One form of controlled release formulation contains the active agent dispersed or encapsulated in a slowly degrading, non-toxic, non-antigenic polymer such as copoly (lactic/glycolic) acid, as described in the pioneering work of Kent, Lewis, Sanders, and Tice, U.S. Pat. No. 4,675,189. The active agent or, preferably, relatively insoluble salts, may also be formulated in cholesterol or other lipid matrix pellets, or silastomer matrix implants. Additional slow release, depot implant or injectable formulations will be apparent to the skilled artisan. See, for example, *Sustained and Controlled Release Drug Delivery Systems*, J. R. Robinson ed., Marcel Dekker, Inc., New York, 1978, and R. W. Baker, *Controlled Release of Biologically Active Agents*, John Wiley & Sons, New York, 1987.

Nasal solutions of the active agent alone or in combination with other pharmaceutically acceptable excipients can also be administered. When formulated for nasal administration, the absorption across the nasal mucous membrane may be enhanced by surfactant acids, such as for example, glycocholic acid, cholic acid, taurocholic acid, ethocholic acid, deoxycholic acid, chenodeoxycholic acid, dehydrocholic acid, glycodeoxycholic acid, cyclodextrins and the like in an amount in the range between about 0.2 and 15 weight percent, preferably between about 0.5 and 4 weight percent, most preferably about 2 weight percent.

Formulations of the active agent may also be administered to the respiratory tract as an aerosol or solution for a nebulizer, or as a microfine powder for insufflation, alone or in combination with an inert carrier such as lactose. In such a case, the particles of the formulation have diameters of less than 50 microns, preferably less than 10 microns.

Non-Pharmaecutical Utilities

The invention also relates to methods and kits for the diagnosis of tyrosine kinase modulated disorders, such as cancer and genetic or congenital immunodeficiency, corresponding to size mutations in the Lck gene. Through use of a kit of the present invention, a patient's Lck binding protein gene is isolated by immunologic assay using anti-LckBP1 protein or anti-LckBP1 fragment or through hybridization to a PCR primer, its DNA sequence is determined and compared to normal gene sequence, and its size determined and compared to normal gene size. Confirmation of gene DNA sequence mutation and/or size mutation indicates that Lck binding-related deficiency is associated with the disease process. Identification of the primer or antibody to which the patient's gene binds is also indicative that treatment with LckBP1, one of its analogs or protein fragments (and which analog or fragment or combination) will be most effective.

Such diagnostic kits include a series of PCR primers with 20- to 30-mer DNA sequences obtained from the full DNA sequence of LckBP1, such as any of SEQ ID NOS:1, 9–12 and 29. Alternatively, the kits may include monoclonal or polyclonal antibodies raised to the LckBP1 protein or fragments.

Still another aspect of the invention entails transgenic animals, such as mice and rats, transfected to overespress LckBP1 or transfected to express no LckBP1. The transgenic animals of the invention are obtained by transfection using the LckBP1 DNA of the invention or fragments thereof, according to the methods described, e.g., in Manipulating the Mouse Embryo, A Laboratory Manual, Hogan et al., Cold Spring Harbor laboratory (1986).

EXAMPLES

The following examples are given to enable those skilled in the art to more clearly understand and to practice the present invention. They should not be considered as limiting the scope of the invention, but merely as being illustrative and representative thereof.

Example 1

Construction of Probe Proteins cDNA fragments for Lck C, Lck N, Lck SH3, Lck SH2, and Lck kinase domains were generated by polymerase chain reactions (PCR). 5' primers contained a BamHI site, whereas the 3' primers contained an EcoRI site.

Lck C and Lck N

| | | |
|---|---|---|
| 5' primer: | 5'-GGGGGGATCCATGGGCTGTGTCTGCAGCTCAAACCCT-3' | (SEQ ID NO:40) |
| 3' primer: | 3'-GGGGGAATTCTCAAGGCTGGGGCTGGTACTGGCCCTC-5' | (SEQ ID NO:41) |

Lck N (nucleotides 164–613) and Lck C (nucleotides 608–1693) fragments were produced by cutting the PCR product with BamHI and EcoRI restriction enzymes. There was an extra BamHI site (nucleotides 608–613) located at the Lck SH2 domain.

Lck SH3 (nucleotides 347–541)

| | | |
|---|---|---|
| 5' primer: | 5'-GGGGGGATCCCAAAACAACCTGGTTATCGCCCTGCAC-3' | (SEQ ID NO:42) |
| 3' primer: | 3'-GGGGGAATTCTCAAGGTTCAGGCTCCAGGCTGTTTGC-5' | (SEQ ID NO:43) |

Lck SH2 (nucleotides 542–865)

| | | |
|---|---|---|
| 5' primer: | 5'-GGGGGAATTCTGGTTCTTCAAGAATCTGAG-3' | (SEQ ID NO:44) |
| 3' primer: | 3'-GGGGGAATTCTCACCACCATGGTTTCTGGG-5' | (SEQ ID NO:45) |

Lck kinase (nucleotides 866–1693)

| | | |
|---|---|---|
| 5' primer: | 5'-GGGGGGATCCGAGGACGAATGGGAAGTTCCCAG-3' | (SEQ ID NO:46) |
| 3' primer: | 3'-GGGGGGGAATTCTCAAGGCTGGGGCTGGTACTGGCCCTC-5' | (SEQ ID NO:47) |

The resulting PCR fragments were cut with site-specific restriction enzymes, and fragments were subcloned into a pGEX-2T (Pharmacia) expression vector. The expression and purification of GST fusion proteins were essentially as described by Smith and Johnson Gene, 67, 31–40 (1988). NM522 host cells carrying pGST-Lck plasmids (Lck C, Lck N, Lck SH3, Lck SH2, or Lck kinase), were grown in L-broth (containing 100 mg/ml of ampicillin) at 37° C. to an absorbance at 550 nm of 0.6. After growth, 0.1 mM of IPTG was added to the medium, and bacterial growth was continued overnight at 20° C. Cells were centrifuged, the cell pellet was suspended in Buffer A (50 mM Tris-HCl pH 8.0, 0.5 mM MgCl$_2$, 5% [v/v] glycerol, 10 mg/ml aprotinin, and 0.1 mM dithiothreitol) containing 1 mg/ml of lysozyme. Samples were kept on ice for 1 hr, then frozen and thawed twice. After the addition of EDTA (final concentration, 1 mM) and NP-40 (final concentration, 0.5% [v/v]), the cell suspensions were sonicated 5 times for 1 min on ice. The resulting solution was centrifuged at 12000 rpm for 10 min, and the supernatant was loaded on a glutathione-Sepharose column (Pharmacia). The column was washed with 10 bed volumes of phosphate-buffered saline (137 mM NaCl, 2.7 mM KCl, and 10 mM potassium phosphate buffer, pH 7.2). GST-Lck fusion protein was then eluted with 10 bed volumes of elution buffer (5 mM glutathione, 50 mM Tris-HCl, pH 8.0).

Example 2

Construction of LckBP1 Mutants

The LckBP1 domains obtained in Example 1 were amplified using PCR. The amplified fragments were digested with BamHI and EcoRI and subcloned into the pGEX-2T vector.

The following primers were used to generate the LckBP1 mutants:

| | | |
|---|---|---|
| 5' primer #1: | 5'GGGGGGATCCATGGAGGCCCCAACCACGGCGTA-3' | (SEQ ID NO:48) |
| 5' primer #2: | 5'-GGGGGGATCCGAGCCAGTGTACGAAGCAGCA-3' | (SEQ ID NO:49) |
| 5' primer #3: | 5'-GGGGGGATCCTATGAGGATGTTGGGGAGTTAG-3' | (SEQ ID NO:50) |
| 5' primer #4: | 5'-GGGGGGATCCGCTATAGCCCTGTATGATTAC-3' | (SEQ ID NO:51) |
| 5' primer #5: | 5'-GGGGGGATCCATGAGCCGAGAAGTCCAGCAG-3' | (SEQ ID NO:52) |
| 5' primer #6: | 5'-GGGGGGATCCGTCTGGCCTCCAGCAGAGAGT-3' | (SEQ ID NO:53) |
| 5' primer #7: | 5'-GGGGGGATCCCAGAATCACTTGGAGGACAAC-3' | (SEQ ID NO:54) |
| 5' primer #8: | 5'-GGGGGGATCCGAAGGCCTCCAGGTGGTGGAAG-3' | (SEQ ID NO:55) |
| 3' primer #1: | 5'-GGGGGAATTCTCATTAGAGGAGCTTGACATAGT-3' | (SEQ ID NO:56) |
| 3' primer #2: | 5'-GGGGGAATTCCTAGGCTATAGCAGAGATCCC-3' | (SEQ ID NO:57) |
| 3' primer #3: | 5'-GGGGGAATTCATTCCACCACCTGGAGGCCTTC-3' | (SEQ ID NO:58) |
| 3' primer #4: | 5'-GGGGGAATTCACAATGGAGACTGCCTCGTGGG-3' | (SEQ ID NO:59) |
| 3' primer #5: | 5'-GGGGGAATTCACTGCTGGACTTCTCGGCTCAT-3' | (SEQ ID NO:60) |
| 3' primer #6: | 5'-GGGGGAATTCACTCTGAGGAGATCTTCTTGGG-3' | (SEQ ID NO:61) |
| 3' primer #7: | 5'-GGGGGAATTCACAATGGAGACTGCCTCGTGGG-3' | (SEQ ID NO:62) |
| 3' primer #8: | 5'-GGGGGAATTCATTCCACCACCTGTAGGCCTTC-3' | (SEQ ID NO:63) |
| 3' primer #9: | 5'-GGGGGAATTCACTCATAGTCAGGCTCTGTCTC-3' | (SEQ ID NO:64) |

The LckBP1 mutants were produced using the primer combinations as follows:

| | | |
|---|---|---|
| LckBP1-#1 | (nucleotides 643–1458), | 5' primer #1 and 3' primer #1; |
| LckBP1-#2 | (nucleotides 643–1308), | 5' primer #1 and 3' primer #2; |
| LckBP1-#3 | (nucleotides 643–1080), | 5' primer #1 and 3' primer #3; |
| LckBP1-#4 | (nucleotides 643–1005), | 5' primer #1 and 3' primer #4; |
| LckBP1-#5 | (nucleotides 643–840), | 5' primer #1 and 3' primer #5; |
| LckBP1-#6 | (nucleotides 1081–1458), | 5' primer #2 and 3' primer #1; |
| LckBP1-#7 | (nucleotides 1162–1458), | 5' primer #3 and 3' primer #1; |
| LckBP1-#8 | (nucleotides 1300–1458), | 5' primer #4 and 3' primer #1; |
| LckBP1-P1 | (nucleotides 820–903), | 5' primer #5 and 3' primer #6; |
| LckBP1-P2 | (nucleotides 904–1005), | 5' primer #6 and 3' primer #7; |
| LckBP1-P3 | (nucleotides 1006–1080), | 5' primer #7 and 3' primer #8; and |
| LckBP1-P4 | (nucleotides 1060–1167), | 5' primer #8 and 3' primer #9. |

Example 3

Construction and screening of cDNA library

Cytoplasmic mRNA of KKF cells was used as a cDNA source. Single-stranded cDNA were generated by reverse transcriptase using a random hexamer (Pharmacia). After second-strand synthesis, EcoRI/Not I adapters were added to both ends of the double-stranded cDNA. The cDNA were inserted into λgt11 phage arms, and phage DNAs were packaged in vitro.

To screen the library, λgt11 phage were plated at a density to produce $4 \times 10^4$ plaques per 150 mm agarose plate. Twenty plates were screened initially. After incubation for 4 hr at 42° C., the plates were overlaid with nitrocellulose filters presoaked in 20 mM isopropyl-β-D-galactopyranoside ("IPTG") (as described by Macgregor et al., 1990 Oncogene, 5, 451–458). Incubation was continued for 4 hr at 37° C. The filters were then removed, washed with TBST at 4° C., and blocked in TBST containing 5% skim milk for 30 min at 4° C. After blocking, the GST-Lck probe was added at a concentration of 1.0 mg/ml, and incubation was continued overnight. Filters were washed 3 times with TBST and incubated with anti-GST antibody at a dilution of 1:800 for 1 hr at 4° C. After washing with TBST 3 times, alkaline phosphatase-conjugated anti-rabbit IgG was added at a dilution of 1:1000 for 30 min at 4° C. GST-Lck fusion protein was detected by incubation of the membrane with anti-GST antibody (⅛₀₀) followed by incubation with alkaline phosphatase-conjugated anti-rabbit (DAKO; ¹⁄₁₀₀₀ dilution) in alkaline phosphatase reaction solution (0.5 mM MgCl2 and 25 mM Na2CO3 [pH 9.8], containing 0.4 mM of nitroblue tetrazolium and 0.4 mM 5-bromo-4-chloro-3-indolylphosphate-p-toluidine salt (Wako Junyaku). Through use of the foregoing screen, the gene encoding partial LckBP1 was obtained.

Example 4

Lysogen of LckBP1

The lysogen carrying the λgt11 phage with the LckBP1 gene was induced with IPTG, and the induced and uninduced proteins were fractionated by SDS-PAGE, and transferred to nitrocellulose filter. The β-gal-LckBP1 fusion protein was detected by incubation of the nitrocellulose membrane with rabbit anti-β-gal antibody (Cappel, ¹⁄₁₀₀₀ dilution), followed by alkaline phosphatase-conjugated anti-rabbit antibody. The LckBP1 protein fragments thus obtained were visualized by incubation of the membrane with alkakine phosphatase reaction solution.

Example 5

Isolation of an LckBP1 clone

We used the west-western technique to isolate a molecule (partial LckBP1) that associates with the SH3 domain of Lck. The pGEX-2T bacterial expression vector was used to produce a fusion protein containing the SH3 domain fused with glutathione S-transferase (GST). This fusion protein, termed GST-LckN, was used to screen a λgt11 cDNA expression library obtained from the murine pre-T cell line KKF, which represents early stage thymocytes and expresses CD4, CD8, and the TCR β chain on the cell surface (Punt et al., 1991 *J. Exp. Med.*, 174, 775–783). After induction of the λgt11 recombinant protein from the cDNA library, proteins were transferred to nitrocellulose filters. Filters were hybridized with GST-LckN, and association of λgt11-derived recombinant proteins with the protein probe was detected by an anti-GST antibody. After three rounds of screening 1×10$^6$ independent phage clones, one clone (partial LckBP1) was isolated. An additional round of amplification of the original cDNA library and screening with the same probe revealed several positive clones, all of which proved to be identical the initial clone, confirming the reliability and reproducibility of our screening conditions.

Example 6

The partial LckBP1 is a Lck SH3 binding protein

Figure 6:
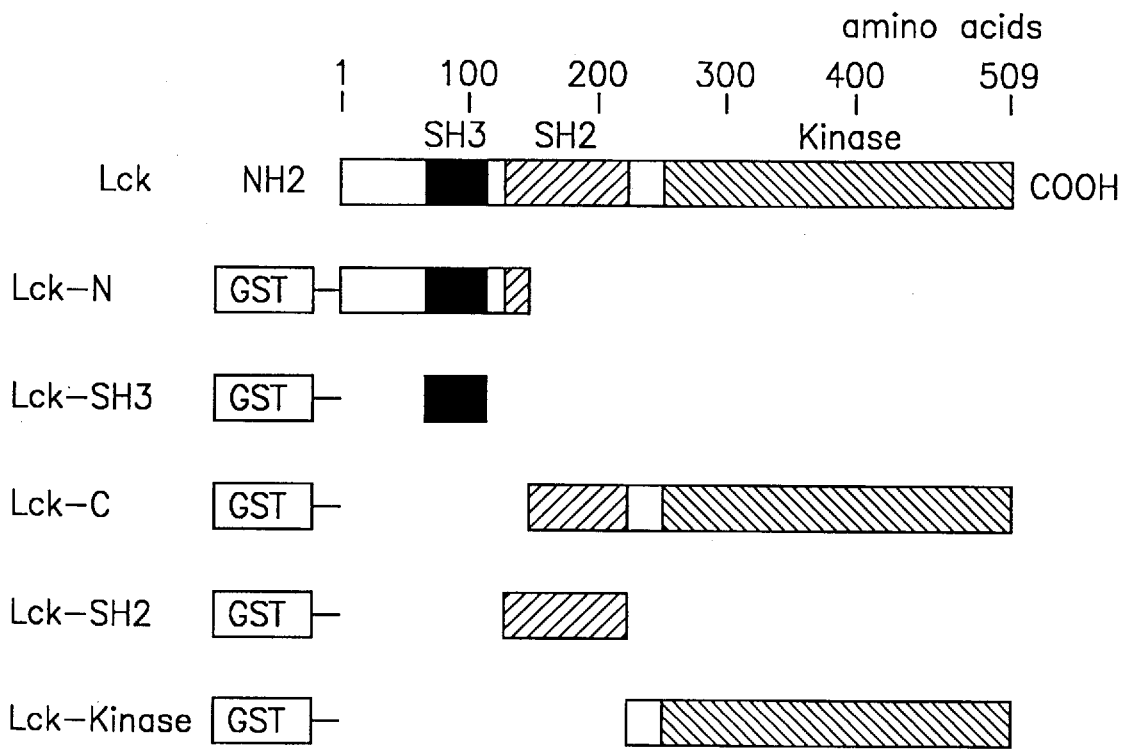
FIG. 6 is a schematic representation of the deletion mutants of Lck, showing the SH3 domain (closed box), the SH2 domain (stripped box), and the kinase domain (shaded box).

A series of Lck deletion mutants were constructed (schematically represented in FIG. 6A) and used to confirm the association between Lck SH3 and partial LckBP1, and to analyze the binding domain of these proteins. DNA fragments were obtained by PCR and the DNA fragments obtained were subcloned into the pGEX-2T vector. The GST-fusion proteins produced in *E. coli*. were separated by SDS-PAGE, transferred to a nitrocellulose filter, and probed with anti-GST antibody. The bands detected indicate production of the desired fusion proteins. (Several different sized bands were also resolved, which, as those skilled in the art will appreciate, is not uncommon in recombinant proteins produced in bacteria.) To examine the association between Lck and LckBP1, we used lysogen to produce LckBP1 as a fusion form of β-gal. Protein lysates of lysogen, with or without IPTG induction of protein production, were separated by SDS-PAGE and transferred to nitrocellulose filters. The association potential of LckBP1 with a series of deletion-Lck proteins was analyzed by probing the LckBP1-transferred filters with the series of deleted GST-Lck fusion proteins (shown in FIG. 6A). GST-LckN (containing SH3) and GST-SH3 protein probes detected a 160-kD protein in the lane containing IPTG-induced lysogen. The 160-kD protein was identified as β-gal-LckBP1 fusion protein, as confirmed by detection of this band by anti-β-gal antibody. The additional bands in the lanes from induced and non-induced lysogen, were observed in all lanes probed with GST-LckC (containing SH2 and kinase domains), GST-SH2, GST-kinase and even with GST included as a negative control, and were thus attributed to nonspecific binding. These results confirmed that the partial LckBP1 binds to the SH3 region in Lck.

Example 7

Isolation of LckBP1 cDNA

Partial LckBP1 cDNA (containing 1385 bp) obtained from the λgt 11 clone was subcloned into plasmid pUC18 and sequenced. The orientation of the partial cDNA was determined by direct DNA sequencing of LckBP1-λgt11 phage DNA. The LckBP1 cDNA sequence showed a strong similarity with the C-terminal region of the human hematopoietic-specific protein 1, HS1 (Kitamura et al., 1989 *Nucleic Acids Res.*, 17, 9367–9379), and the chicken Src substrate p80/85 (Wu et al., 1991 *Mol. Cell. Biol.*, 11, 5113–5124). To isolate the full-length cDNA of the LckBP1 gene, we used the 5'-RACE system (GIBCO-BRL), in which dC-tailed cDNA is generated from the primers based on the gene-specific defined DNA sequence, and subsequently amplified by PCR between the anchor primer and nested gene-specific primer.

Using KKF cell RNA, a full-length cDNA was obtained. First-strand cDNA was synthesized from cytoplasmic mRNA of KKF cells using a LckBP1 specific primer [5'-AGTCTCCCTCTGCATCC-3', nucleotides 1197–1213 (SEQ ID NO:65)] made from the confirmed partial sequence. The 3' end of the cDNA was tailed with dCTP using terminal deoxynucleotidyl transferase (TdT). The resulting cDNA was amplified by PCR using the 5' primer 5'-CUACUACUACUAGGCCACGCGTCGACTAGTAC-GGGIIGGGIIGGGIIG-3' (SEQ ID NO:66) and 3' primer 5'-CAUCAUCAUCAUGCCAACAGCACTCTTATCCAC-3' (nucleotides, 613–633) (I, inosine; U, uridine) (SEQ ID NO:67) also made from the confirmed partial sequence. The PCR product containing uridine was digested with uracil DNA glycosylase (UDG, GIBCO-BRL) to remove uracil. The UDG-treated cDNA was annealed with pAMPI plasmid (GIBCO-BRL) and transformed into JM109 cells. The sequence was determined according to Sanger's methods (1977). Sequence analysis of this full-length cDNA revealed a 1458bp open reading frame [i.e., base pairs 61 to 1518 (SEQ ID NO:68)] in the total 2003bp (FIG. 1). The open reading frame encodes a protein (LckBP1) having 486 amino acids (SEQ ID NO:2) (FIG. 1) the predicted molecular mass of which is 54 kDa.

Example 8

LckBP1-#1

8A. Construction of LckBP1-#1

The PCR fragment of LBP1#1 was digested with BamHI and EcoRI restriction enzymes, and was subcloned into a BamHI-EcoRI site of pGEX-2T (Pharmacia) expression vector. The ligation and transformation conditions were essentially as described by Sambrook, Fritsch and Maniatis, Molecular Cloning: a laboratory manual, Second Edition (Cold Spring Harbor Laboratory Press, New York) 1989. 20ng of the PCR fragment and pGEX-2T were incubated with 0.5 Wiss unit of bacteriophage T4 DNA ligase [50 mM Tris-HCl, pH 7.6; 10 mM MgCl$_2$; 10 mM dithiothreitol; 50 μg/ml bovine serum albumin (Fraction V; Sigma); 1 mM ATP] at 16° C. for 1 hour. The resulting reaction mixture was mixed with 500 μl of SOB broth [20 g bacto-tryptone, 5 g of bacto-yeast extract, and 0.5 g of NaCl per liter (pH 7.0) containing 10 mM MgCl$_2$]. The sequence of joint region between GST gene and LckBP1 PCR fragment was confirmed by Sanger's method (Sanger et al., *Proc. Natl. Acad. Sci. USA* 74, 5463–5467).

8B. LckBP1-#1 protein Expression

The expression and purification was performed essentially as described by Smith and Johnson (1988 *Gene*, 67, 31–40). NM522 host cells carrying pGST-LBP1-#1 plasmids were grown in L-broth (10 g bacto-tryptone, 5 g of bacto-yeast extract, and 5 g of NaCl per liter containing 100 μg/ml of ampicillin) at 37° C. to an absorbance at 550 nm of 0.6. After growth, 0.1 mM of IPTG was added to the medium, and bacterial growth was continued overnight at 20° C. Cells were centrifuged, the cell pellet was suspended in Buffer A (50 mM Tris-HCl pH 8.0, 0.5 mM MgCl$_2$, 5% [v/v] glycerol, 10 μg/ml aprotinin, and 0.1 mM dithiothreitol) containing 1 mg/ml of lysozyme. Samples were kept on ice for 1 hour, then frozen and thawed twice. After the addition of EDTA (final concentration, 1 mM) and NP-40 (final concentration, 0.5% [v/v]), the cell suspensions were sonicated 5 times for 1 minute on ice. The resulting solution was centrifuged at 12000 rpm for 10 minutes, and the supernatant was loaded on a glutathione-Sepharose column (Pharmacia). The column was washed with 10 bed volumes of phosphate-buffered saline (137 mM NaCl, 2.7 mM KCl, and 10 mM potassium phosphate buffer, pH 7.2). GST-LckBP1-#1 fusion protein was then eluted with 10 bed volumes of elution buffer (5 mM glutathione, 50 mM Tris-HCl, pH 8.0).

8C. Antibody Recognition

The GST-specific antibody was generated in a rabbit immunized with GST protein, and used to detect GST. The LckBP1-specific antibody was generated in a rabbit immunized with GST-LckBP1-#4 (amino acids 215–355 of LckBP1) and used to detect LckBP1-#1.

The GST and LckBP1-#1 fused to GST (30 ng) proteins were fractionated by SDS-PAGE and transferred to nitrocellulose filter, and probed with anti-LckBP1 antibody (⅓₆₀₀ dilution) followed by incubation with alkaline phosphatase-conjugated anti-rabbit antibody (DAKO; ⅟₁₀₀₀ dilution). Anti-LckBP1 antibody recognized LckBP1-#1, specifically.

8D. LckBP1

By following the procedures of parts A, B and C above, substituting the fragment LckBP1-#1 with the full length cDNA of SEQ ID NO:1 there is obtained full length LckBP1 protein of SEQ ID NO:2.

Example 9

Expression of LckBP1 in Various Cell Lines

The LckBP1 antigen is expressed not only in the pre-T cell line KKF, but also in the mature T cell line 2B4. To analyze the expression pattern of LckBP1 in various cell lines, we performed Western blot analysis using cell lysates separated by SDS-PAGE, transferred to nitrocellulose filters, and probed with anti-LckBP1 antibody or anti-GST antibody. Expression of p85 was observed in the murine transformed T cell lines NCKA (TCR⁻), KgV (TCRαβ⁺), and ARK1 (TCRαβ⁺). In addition, p85 expression was detected in the B cell lymphoma WEHI231, but not in NIH3T3 cells or BALB/3T3 clone A31, whereas p80 was expressed in all cell lines examined. These results indicate that p85 is expressed in a hematopoietic-specific manner, while p80 is expressed ubiquitously. The filter probed with anti-GST antibody showed some background proteins, representing non-specific binding.

Example 10

Characterization of Lck SH3 Binding Sites of LckBP1

The partial LckBP1 phage clone initially isolated contains the C-terminal region (amino acids 187–486) of LckBP1. Since this clone was isolated as a gene encoding a protein that associates with the Lck-SH3 region, the SH3 domain in Lck was expected to associate with the protein produced by the initial λgt 11 clone, that is, the LckBP1 C-terminal region. To analyze the Lck-SH3 binding site in the LckBP1 C-terminal region, we constructed a series of deletion mutants of the LckBP1 C-terminal region.

Figure 7:
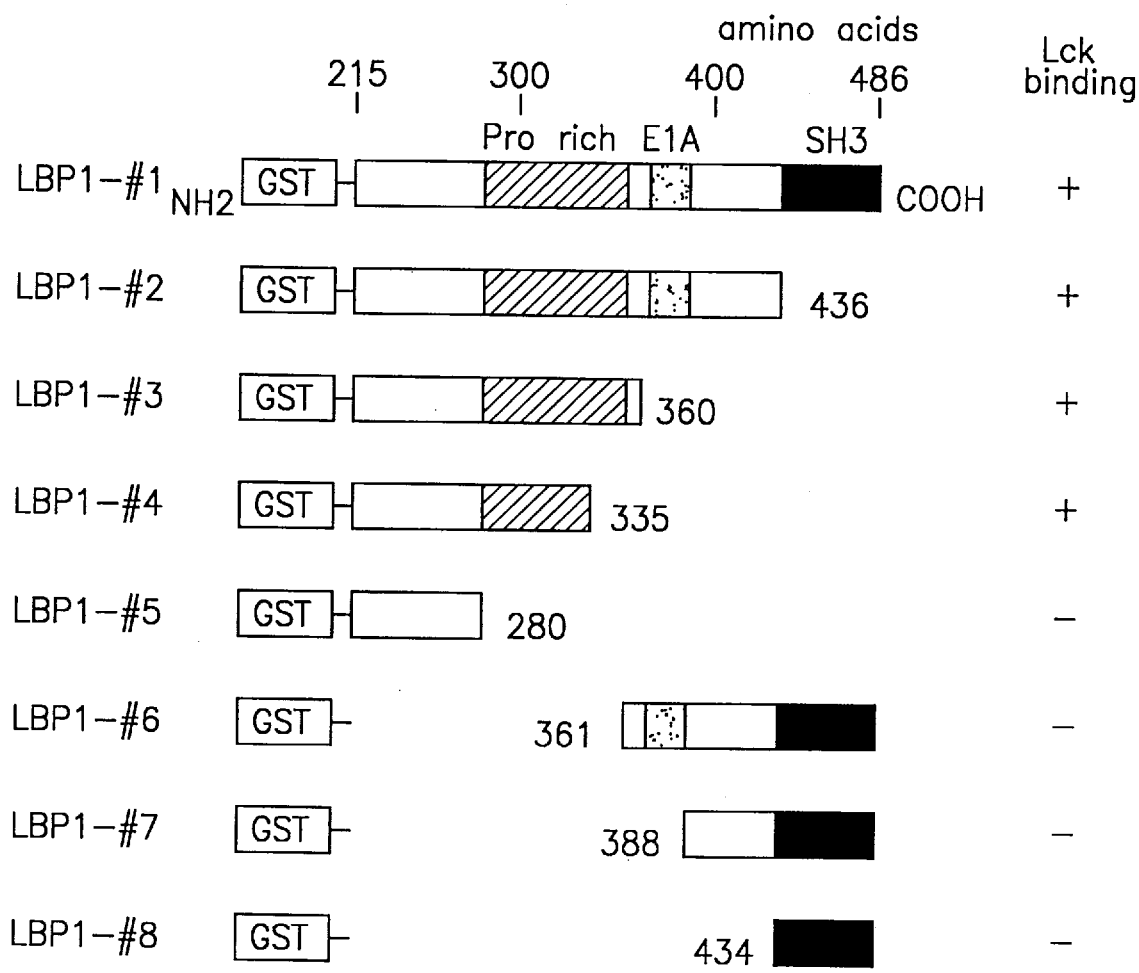
FIG. 7 illustrate the location of the Lck SH3 domain binding site on LckBP1.

DNA deletion fragments were obtained by PCR, and subcloned into the pGEX-2T vector (FIG. 7). The fusion proteins produced in *E. coli* were subjected to SDS-PAGE, transferred to a nitrocellulose filter, and probed with biotinylated GST or GST-Lck SH3 protein. The biotinylated GST-Lck SH3 protein recognized mutants #1 (amino acids 215–486), #2 (amino acids 215–436), #3 (amino acids 215–360), #4 (amino acids 215–335), but not mutants #5 (amino aids 215–280), #6 (amino acids 361–486), #7 (amino acids 388–486), and #8 (amino acids 434–486). The biotinylated GST probe did not recognize any strong bands. Biotinylation of both probes was confirmed by Western blot analysis using alkaline phosphatase-conjugated streptavidin as probe.

This analysis of LckBP1 deletion mutants revealed Lck binding regions in LckBP1. Lck bound to LckBP1-mutant #4 but not #5, indicating that the Lck binding region is located in one of the proline-rich regions (amino acids 281–335). The other proline-rich region extends from 336 to 360 amino acids in LckBP1 (which includes the PPALPPRTP, a typical proline-rich region-containing a potential MAP kinase phosphorylation site). Analysis of these five mutants was inconclusive about the role of the second proline-rich region in Lck binding.

Example 11

Generation of Peptide Fragments And Determination of Lck Binding to the Second Proline-rich Region of LckBP1

Generation of Fragments

To localize the Lck SH3 binding region more precisely and to determine whether Lck binds to the second proline-rich region, we generated three short fragments obtained from this region (FIG. 5) P1, P2 and P3 representing amino acid 274 to 301, 302 to 335, and 336 to 360, respectively, and analyzed their Lck-binding potential. P3 contains a potential MAP kinase phosphorylation site (boxed in FIG. 5). An additional fragment (P4) was generated covering the proline-rich region (amino acids 354–390), which is located in the E1A region, and was used to confirm the non-specificity of the smaller sized bands detected in GST-LckBP1-#6. DNA fragments were obtained by PCR and subcloned into the pGEX-2T vector. Proteins produced in *E. coli* were separated by SDS-PAGE, blotted to nitrocellulose filters, and probed with biotinylated GST or GST-LckSH3 protein. The peptide fragments had the following sequences:

| P1 | Met | Ser | Arg | Glu | Val | Gln | Gln | Pro | Ser | Met | Pro | Val | Glu | Glu | Pro | Ala |
|---|---|---|---|---|---|---|---|---|---|---|---|---|---|---|---|---|
| | Ala | Pro | Ala | Gln | Leu | Pro | Lys | Lys | Ile | Ser | Ser | Glu | | | | |
| | (SEQ ID NO:9) | | | | | | | | | | | | | | | |
| P2 | Val | Trp | Pro | Pro | Ala | Glu | Ser | His | Leu | Pro | Pro | Glu | Ser | Gln | Pro | Val |
| | Arg | Ser | Arg | Arg | Glu | Tyr | Pro | Val | Pro | Ser | Leu | Pro | Thr | Arg | Gln | Ser |
| | Pro | Leu | | | | | | | | | | | | | | |
| | (SEQ ID NO:10) | | | | | | | | | | | | | | | |
| P3 | Gln | Asn | His | Leu | Glu | Asp | Asn | Glu | Glu | Pro | Pro | Ala | Leu | Pro | Pro | Arg |
| | Thr | Pro | Glu | Gly | Leu | Gln | Val | Val | Glu | | | | | | | |
| | (SEQ ID NO:11) | | | | | | | | | | | | | | | |
| P4 | Glu | Gly | Leu | Gln | Val | Val | Glu | Glu | Pro | Val | Tyr | Glu | Ala | Ala | Pro | Glu |
| | Leu | Glu | Pro | Glu | Pro | Glu | Pro | Asp | Tyr | Glu | Pro | Glu | Pro | Glu | Thr | Glu |
| | Pro | Asp | Tyr | Glu | | | | | | | | | | | | |
| | (SEQ ID NO:12) | | | | | | | | | | | | | | | |

Lck Binding Results

Biotinylated GST-LckSH3 protein bound to mutant P2 but not to P1. Lck SH3 also bound to the mutant P3. Although the amino acid sequence in the P2 fragment is not well conserved among HS1 and coatactin family proteins, two prolines (double underlined in FIG. 5) are well conserved among these proteins. Thus this region around the two conserved prolines, is a Lck binding site. Note that the P3 fragment contains the potential MAP kinase recognition site (boxed in FIG. 5). The absence of binding of the P4 fragment to the Lck-SH3 probe confirmed that Lck does not bind to the proline-glutamate region.

Alternative Peptide Fragments

Similarly, by recombinant methodology known to those skilled in the art, and substituting, e.g., one or more Ser with Thr, Leu with Ser, Thr with Ile, and/or Thr with Ser, and/or replacing the one or more amino acids in the murine (LckBP1) sequence with the corresponding amino acid(s) (or deleting the LckBP1 amino acid where there is no corresponding amino acid or where substituting the corresponding amino acid would constitute a non-conservative change, such as between Leu and Pro) in the human (HS1) sequence, for example, there are obtained the following peptides (wherein substituted amino acids are indicated by underlining) having Lck binding activity.

| | | | | | | | | | | | | | | | | |
|---|---|---|---|---|---|---|---|---|---|---|---|---|---|---|---|---|
| P2A | Val | Trp | Pro | Pro | Ala | Glu | Ser | His | Leu | Pro | Pro | Glu | Ser | Gln | Pro | Val |
| | Arg | <u>Thr</u> | Arg | Arg | Glu | Tyr | Pro | Val | Pro | Ser | Leu | Pro | Thr | Arg | Gln | Ser |
| | Pro | Leu | | | | | | | | | | | | | | |
| | (SEQ ID NO:13) | | | | | | | | | | | | | | | |
| P2B | Val | Trp | Pro | Pro | Ala | Glu | Ser | His | Leu | Pro | Pro | Glu | Ser | Gln | Pro | Val |
| | Arg | Ser | Arg | Arg | Glu | Tyr | Pro | Val | Pro | <u>Leu</u> | Leu | Pro | Thr | Arg | Gln | Ser |
| | Pro | Leu | | | | | | | | | | | | | | |
| | (SEQ ID NO:14) | | | | | | | | | | | | | | | |
| P2C | Val | Trp | Pro | Pro | Ala | Glu | Ser | His | Leu | Pro | Pro | Glu | Ser | Gln | Pro | Val |
| | Arg | Ser | Arg | Arg | Glu | Tyr | Pro | Val | Pro | Ser | Leu | Pro | <u>Ile</u> | Arg | Gln | Ser |
| | Pro | Leu | | | | | | | | | | | | | | |
| | SEQ ID NO:15) | | | | | | | | | | | | | | | |
| P2D | Val | Trp | Pro | Pro | Ala | Glu | Ser | His | Leu | Pro | Pro | Glu | Ser | Gln | Pro | Val |
| | Arg | Ser | Arg | Arg | Glu | Tyr | Pro | Val | Pro | Ser | Leu | Pro | Thr | Arg | Gln | <u>Thr</u> |
| | Pro | Leu | | | | | | | | | | | | | | |
| | (SEQ ID NO:16) | | | | | | | | | | | | | | | |
| P2E | Val | Trp | Pro | Pro | Ala | Glu | Ser | His | Leu | Pro | Pro | Glu | Ser | Gln | Pro | Val |
| | Arg | Ser | Arg | Arg | Glu | Tyr | Pro | Val | Pro | Ser | Leu | Pro | Thr | Arg | Gln | Ser |
| | (SEQ ID NO:17) | | | | | | | | | | | | | | | |
| P2F | Val | Trp | Pro | Pro | Ala | Glu | Ser | His | Leu | Pro | Pro | Glu | Ser | Gln | Pro | Val |
| | Arg | <u>Thr</u> | Arg | Arg | Glu | Tyr | Pro | Val | Pro | <u>Leu</u> | Leu | Pro | <u>Ile</u> | Arg | Gln | <u>Thr</u> |
| | Pro | Leu | | | | | | | | | | | | | | |
| | (SEQ ID NO:18) | | | | | | | | | | | | | | | |
| P2G | Val | Trp | Pro | Pro | Ala | Glu | Ser | His | Leu | Pro | Pro | Glu | Ser | Gln | Pro | Val |
| | Arg | Ser | Arg | Arg | Glu | Tyr | Pro | Val | Pro | <u>Leu</u> | Leu | Pro | Thr | Arg | Gln | <u>Thr</u> |
| | Pro | Leu | | | | | | | | | | | | | | |
| | (SEQ ID NO:19) | | | | | | | | | | | | | | | |
| P2H | Val | Trp | Pro | Pro | Ala | Glu | Ser | His | | Pro | Pro | Glu | Ser | Gln | Pro | Val |
| | Arg | Ser | Arg | Arg | Glu | Tyr | Pro | Val | Pro | <u>Leu</u> | Leu | Pro | <u>Ile</u> | Arg | Gln | Ser |
| | Leu | | | | | | | | | | | | | | | |
| | (SEQ ID NO:20) | | | | | | | | | | | | | | | |
| P2I | Val | Trp | Pro | Pro | <u>Val</u> | <u>Gly</u> | <u>Thr</u> | <u>Pro</u> | <u>Pro</u> | <u>Ser</u> | <u>Ser</u> | Glu | Ser | Gln | Pro | Val |
| | Arg | Ser | Arg | Arg | Glu | Tyr | Pro | Val | Pro | Ser | Leu | Pro | Thr | Arg | Gln | Ser |
| | Pro | Leu | | | | | | | | | | | | | | |
| | (SEQ ID NO:21) | | | | | | | | | | | | | | | |
| P3A | Gln | Asn | His | | Glu | Asp | Asn | Glu | Glu | Pro | Pro | Ala | Leu | Pro | Pro | Arg |
| | Thr | Pro | Glu | Gly | Leu | Gln | Val | Val | Glu | | | | | | | |
| | (SEQ ID NO:22) | | | | | | | | | | | | | | | |
| P3B | Gln | Asn | His | Leu | Glu | Asp | Asn | Glu | Glu | Pro | Pro | Ala | Leu | Pro | Pro | Arg |
| | Thr | | Glu | Gly | Leu | Gln | Val | Val | Glu | | | | | | | |
| | (SEQ ID NO:23) | | | | | | | | | | | | | | | |
| P3C | Gln | Asn | His | | Glu | Asp | Asn | Glu | Glu | Pro | Pro | Ala | Leu | Pro | Pro | Arg |
| | Thr | | Glu | Gly | Leu | Gln | Val | Val | Glu | | | | | | | |
| | (SEQ ID NO:24) | | | | | | | | | | | | | | | |
| P3D | Gln | Asn | His | Leu | Glu | Asp | Asn | Glu | Glu | Pro | Pro | Ala | Leu | Pro | Pro | Arg |
| | <u>Ser</u> | Pro | Glu | Gly | Leu | Gln | Val | Val | Glu | | | | | | | |
| | (SEQ ID NO:25) | | | | | | | | | | | | | | | |
| P3E | Gln | Asn | His | Leu | Glu | Asp | Asn | Glu | Glu | Pro | Pro | Ala | <u>Ser</u> | Pro | Pro | Arg |
| | Thr | Pro | Glu | Gly | Leu | Gln | Val | Val | Glu | | | | | | | |
| | (SEQ ID NO:26) | | | | | | | | | | | | | | | |
| P3F | | | His | Leu | Glu | Asp | Asn | Glu | Glu | Pro | Pro | Ala | Leu | Pro | Pro | Arg |
| | Thr | Pro | Glu | Gly | Leu | Gln | Val | Val | Glu | | | | | | | |
| | (SEQ ID NO:27) | | | | | | | | | | | | | | | |
| P3G | | | His | | Glu | Asp | Asn | Glu | Glu | Pro | Pro | Ala | Leu | Pro | Pro | Arg |
| | Thr | | Glu | Gly | <u>Ser</u> | Gln | Val | Val | Glu | | | | | | | |
| | (SEQ ID NO:28) | | | | | | | | | | | | | | | |

Example 12

LckBP1-SH3 Protein Fragment

The LckBP1-SH3 region was identified through sequence homology comparixon to other reported SH3 domains. It has the following sequence.

| SH3 | Ala | Ile | Ala | Leu | Tyr | Asp | Tyr | Gln | Gly | Glu | Gly | Ser | Asp | Glu | Leu | Ser |
|---|---|---|---|---|---|---|---|---|---|---|---|---|---|---|---|---|
| | Phe | Asp | Pro | Asp | Asp | Ile | Ile | Thr | Asp | Ile | Glu | Met | Val | Asp | Glu | Gly |
| | Trp | Trp | Arg | Gly | Gln | Cys | Arg | Gly | His | Phe | Gly | Leu | Phe | Pro | Ala | Asn |
| | Tyr | Val | Lys | Leu | Leu | | | | | | | | | | | |
| | (SEQ ID NO:29) | | | | | | | | | | | | | | | |

Alternative Peptide Fragments

Similarly, by recombinant methodology known to those skilled in the art, and substituting, e.g., one or more Ser with Thr, Leu with Ser, Thr with Ile, and/or Thr with Ser. and/or replacing the one or more amino acids in the murine (LckBP1) sequence with the corresponding amino acid(s) (or deleting the LckBP1 amino acid where there is no corresponding amino acid or where substituting the corresponding amino acid would constitute a non-conservative change, such as between Leu and Pro) in the human (HS1) sequence, for example, there are obtained the following peptides (wherein substituted amino acids are indicated by underlining) having Lck binding activity.

| SH3 | Ala | *Val* | Ala | Leu | Tyr | Asp | Tyr | Gln | Gly | Glu | Gly | Ser | Asp | Glu | Leu | Ser |
|---|---|---|---|---|---|---|---|---|---|---|---|---|---|---|---|---|
| | Phe | Asp | Pro | Asp | Asp | Ile | Ile | Thr | Asp | Ile | Glu | Met | Val | Asp | Glu | Gly |
| | Trp | Trp | Arg | Gly | Gln | Cys | Arg | Gly | His | Phe | Gly | Leu | Phe | Pro | Ala | Asn |
| | Tyr | Val | Lys | Leu | Leu | | | | | | | | | | | |
| | (SEQ ID NO:30) | | | | | | | | | | | | | | | |
| SH3B | Ala | Ile | Ala | *Ser* | Tyr | Asp | Tyr | Gln | Gly | Glu | Gly | Ser | Asp | Glu | Leu | Ser |
| | Phe | Asp | Pro | Asp | Asp | Ile | Ile | Thr | Asp | Ile | Glu | Met | Val | Asp | Glu | Gly |
| | Trp | Trp | Arg | Gly | Gln | Cys | Arg | Gly | His | Phe | Gly | Leu | Phe | Pro | Ala | Asn |
| | Tyr | Val | Lys | Leu | Leu | | | | | | | | | | | |
| | (SEQ ID NO:31) | | | | | | | | | | | | | | | |
| SH3C | Ala | Ile | Ala | Leu | Tyr | Asp | Tyr | Gln | Gly | Glu | Gly | Ser | Asp | Glu | Leu | Ser |
| | Phe | Asp | Pro | Asp | Asp | Ile | Ile | *Ile* | Asp | Ile | Glu | Met | Val | Asp | Glu | Gly |
| | Trp | Trp | Arg | Gly | Gln | Cys | Arg | Gly | His | Phe | Gly | Leu | Phe | Pro | Ala | Asn |
| | Tyr | Val | Lys | Leu | Leu | | | | | | | | | | | |
| | (SEQ ID NO:32) | | | | | | | | | | | | | | | |
| SH3D | Ala | Ile | Ala | Leu | Tyr | Asp | Tyr | Gln | Gly | Glu | Gly | Ser | Asp | Glu | Leu | Ser |
| | Phe | Asp | Pro | Asp | Asp | *Val* | Ile | Thr | Asp | Ile | Glu | Met | Val | Asp | Glu | Gly |
| | Trp | Trp | Arg | Gly | Gln | Cys | Arg | Gly | His | Phe | Gly | Leu | Phe | Pro | Ala | Asn |
| | Tyr | Val | Lys | Leu | Leu | | | | | | | | | | | |
| | (SEQ ID NO:33) | | | | | | | | | | | | | | | |
| SH3E | Ala | Ile | Ala | Leu | Tyr | Asp | Tyr | Gln | Gly | Glu | Gly | *Thr* | Asp | Glu | Leu | Ser |
| | Phe | Asp | Pro | Asp | Asp | Ile | Ile | Thr | Asp | Ile | Glu | Met | Val | Asp | Glu | Gly |
| | Trp | Trp | Arg | Gly | Gln | Cys | Arg | Gly | His | Phe | Gly | Leu | Phe | Pro | Ala | Asn |
| | Tyr | Val | Lys | Leu | Leu | | | | | | | | | | | |
| | (SEQ ID NO:34) | | | | | | | | | | | | | | | |
| SH3F | Ala | Ile | Ala | Leu | Tyr | Asp | Tyr | Gln | Gly | Glu | Gly | Ser | Asp | Glu | Leu | Ser |
| | Phe | Asp | Pro | Asp | Asp | Ile | Ile | Thr | Asp | Ile | Glu | Met | Val | Asp | Glu | Gly |
| | Trp | Trp | Arg | Gly | *Arg* | Cys | *His* | Gly | His | Phe | Gly | Leu | Phe | Pro | Ala | Asn |
| | Tyr | Val | Lys | Leu | Leu | | | | | | | | | | | |
| | (SEQ ID NO:35) | | | | | | | | | | | | | | | |
| SH3G | Ala | Ile | Ala | Leu | Tyr | Asp | Tyr | Gln | Gly | Glu | Gly | Ser | Asp | Glu | Leu | Ser |
| | Phe | Asp | Pro | Asp | Asp | Ile | Ile | Thr | Asp | Ile | Glu | Met | Val | Asp | Glu | Gly |
| | Trp | Trp | Arg | Gly | Gln | Cys | Arg | Gly | His | Phe | Gly | Leu | Phe | Pro | Ala | Asn |
| | Tyr | Val | Lys | Leu | Leu | *Glu* | | | | | | | | | | |
| | (SEQ ID NO:36) | | | | | | | | | | | | | | | |
| SH3H | Ala | Ile | Ala | Leu | Tyr | Asp | Tyr | Gln | *Ala* | *Ala* | Gly | Ser | Asp | Glu | Leu | Ser |
| | Phe | Asp | Pro | Asp | Asp | Ile | Ile | Thr | Asp | Ile | Glu | Met | Val | Asp | Glu | Gly |
| | Trp | Trp | Arg | Gly | Gln | Cys | Arg | Gly | His | Phe | Gly | Leu | Phe | Pro | Ala | Asn |
| | Tyr | Val | Lys | Leu | Leu | | | | | | | | | | | |
| | (SEQ ID NO:37) | | | | | | | | | | | | | | | |
| SH3I | Ala | *Val* | Ala | Leu | Tyr | Asp | Tyr | Gln | Gly | Glu | Gly | Ser | Asp | Glu | Leu | Ser |
| | Phe | Asp | Pro | Asp | Asp | *Val* | Ile | Thr | Asp | Ile | Glu | Met | Val | Asp | Glu | Gly |
| | Trp | Trp | Arg | Gly | Gln | Cys | Arg | Gly | His | Phe | Gly | Leu | Phe | Pro | Ala | Asn |
| | Tyr | Val | Lys | Leu | Leu | *Glu* | | | | | | | | | | |
| | (SEQ ID NO:38) | | | | | | | | | | | | | | | |
| SH3J | Ala | Ile | Ala | Leu | Tyr | Asp | Tyr | Gln | Gly | Glu | Gly | *Thr* | Asp | Glu | Leu | *Thr* |
| | Phe | Asp | Pro | Asp | Asp | Ile | *Thr* | *Ile* | Asp | Ile | Glu | Met | Val | Asp | Glu | *Gly* |
| | Trp | Trp | Arg | Gly | Gln | Cys | Arg | Gly | His | Phe | Gly | Leu | Phe | Pro | Ala | Asn |
| | Tyr | Val | Lys | Leu | Leu | | | | | | | | | | | |
| | (SEQ ID NO:39) | | | | | | | | | | | | | | | |

Examples 13–15

These examples illustrate the preparation of a representative pharmaceutical formulations containing LckBP1 and active fragments, including the SH3 region as the Active Agent. The analogous proteins and fragments substituting, e.g., one or more Ser with Thr, Leu with Ser, Thr with Ile, and/or Thr with Ser, and/or replacing the one or more amino acids in the murine (LckBP1) sequence with the corresponding amino acid(s) (or deleting the LckBP1 amino acid where there is no corresponding amino acid or where substituting the corresponding amino acid would constitute a non-conservative change, such as between Leu and Pro) in the human (HS1) sequence (e.g., SEQ ID NOS:2, 10, 11, and 13–39) may also be employed as the Active Agent in any of the examples, adjusting concentration to compensate for molecular size and activity as appropriate.

Example 13

This example illustrates the preparation of a representative pharmaceutical formulation for oral administration.

| Ingredients | Quantity per capsule, mg |
|---|---|
| Active Agent (SEQ ID NO:2) | 1.0 |
| lactose, spray-dried | 247 |
| magnesium stearate | 2 |

The above ingredients are mixed and introduced into a hard-shell gelatin capsule.

Example 14

An injectable preparation buffered to a suitable pH is prepared having the following composition:

| Ingredients | Amount |
|---|---|
| Active Agent (SEQ ID NO:11) | 10.0 µg |
| Sodium Acetate Buffer Solution (0.4 M) | 2.0 ml |
| HCl (1N) or NaOH (1N) | q.s. to suitable pH |
| water (distilled, sterile) | q.s. to 20 ml |

Example 15

A suppository totalling 2.5 grams is prepared having the following composition:

| | |
|---|---|
| Active Agent (SEQ ID NO:29) | 5.0 µg |
| witepsol H-15* | balance |

(*triglycerides of saturated vegetable fatty acid; a product of HULS, Inc., New Jersey).

Example 16

Lck tyrosine kinase associates with LckBP1 in vivo

Anti-LckBP1 polyclonal antibody, obtained by immunization of a rabbit with the GST-LckBP1-#4 fusion protein (FIG. 7, amino acids 215–335), was used for immuno-precipitation of cell lysate form thymocytes. Products were separated by SDS-PAGE, transferred to a nitrocellulose filter, and probed with anti-LckBP1 antibody. Anti-LckBP1 antibody recognized an 85-kDa (p85) protein from the thymocyte lysate. To analyze the in vivo association between Lck and LckBP1, we immuno-precipitated cell lysates obtained from thymocytes with commercially available anti-Lck antibody and immuno-blotted the precipitates with anti-LckBP1 antibody. Anti-LckBP1 antibody detected the p85 band in the immuno-precipitate of anti-Lck antibody. The immuno-precipitation of p85 by the anti-Lck antibody and the detection of p85 in the immuno-precipitate by anti-LckBP1 antibody indicates that Lck and p85 associate in vivo in thymocytes. Immuno-precipitation of KKF and 2B4 cell lysates with anti-LckBP1 or -Lck antibody followed by Western blotting of the precipitates with anti-LckBP1 antibody revealed two major bands, p85 and 80-kDa (p80), in the lysates immuno-precipitated by anti-LckBP1 antibody. The immuno-precipitates of anti-Lck antibody coprecipitated p85 in both KKF and 2B4 cell lysates but not p80 in either lysate. The anti-GST antibody did not detect any major proteins. Thus, Lck tyrosine kinase associates with p8s but not with p80 in vivo, confirming that the LckBP1 of the present invention in fact binds to Lck in vivo. Further, this demonstrates that LckBP1-p85 is expressed only in hematopoetic lineage cells.

Example 17

In Vitro Determination of Therapeutic Activity As an Immunosuppressive Agent Utilizing the Inhibition of IMP Dehydrogenase Assay This assay is a modification of the method of Anderson, J. H. and Sartorelli, A. C., *Jour. Biol. Chem*, 243:4762–4768 (1968). It measures the formation of NADH ($\lambda_{max}$=340 nm, $\epsilon340$=6,220 $M^1cm^{-1}$) as Inosine 5'-monophosphate ("IMP") is converted to Xanthosine 5'-monophosphate ("XMP") by the human Type II IMP dehydrogenase ("IMPDH").

Test compounds are dissolved and diluted in DMSO, and reaction solutions containing compounds at 0, 0.01, 0.10, 1.0, 10, and 100 µM are prepared in disposable methacrylic plastic microcuvets ('UV-transparent' plastic, 1 cm pathlength, 1.5 ml capacity). The solutions (0.5–1 ml) contain the following: 0.1M TrisHCL, pH 8.0; 0.1M KCL; 3.0 mM EDTA; 100 µg/ml BSA; 0.05 mM IMP; 0.10 mM NAD; 10% DMSO; 5–15 nM IMPDH (0.003–0.010 units/ml; one unit of enzyme catalyzes the formation of one µmol NADH per minute at 40° C. at saturating substrate concentrations—200 µM IMP and 400 µM NAD). Reactions are performed at 40° C. and initiated by the addition of enzyme. Mycophenolic acid ($IC_{50}$≈0.02 µM) serves as the positive control. The reactions are monitored at 340 nm for 10 minutes in a UV/VIS spectrophotometer, and rate data are collected.

The 50% inhibitory value ("$IC_{50}$") is determined by fitting the fractional activities relative to control to the following equation on a Macintosh computer by the program Systat:

Fractional activity=MAX/((X/$IC_{50}$)$^n$+1).

X is the concentration of the compound, and the term n accounts for deviations of the data from a simple competitive inhibition model.

LckBP1 and the fragments of the present invention inhibit IMPDH when tested by this method, indicating activity as an immunosuppressive agent.

Example 18

In Vitro Determination of Immunosuppressive Activity Utilizing Responses of Human Peripheral Blood Lymphocytes to Phytohemagglutinin (PHA)

This procedure is a modification of a procedure initially described by Greaves, et al. ["Activation of human T and B lymphocytes by polyclonal mitogens," *Nature*, 248:698–701 (1974)].

Human mononuclear cells ("PBL") are separated from heparinized whole blood by density gradient centrifugation in Ficoll-Plaque (Pharmacia). After washing, $2\times10^5$ cells/well are cultured in microtiter plates with RPMI 1640 supplemented with 5% fetal calf serum, penicillin and streptomycin. PHA (Sigma) at 10 μg/ml is then added. Test materials are tested at concentrations between $10^4$ and $10^3$M, by addition to the culture at time 0. Cultures are set up in quadruplicate and incubated at 37° C. in a humidified atmosphere with 7% $CO_2$ for 72 hours. A pulse of 0.5 μCi/well of $^3$H-thymidine is added for the last 6 hours. Cells are collected on glass fiber filters with an automatic harvester and radioactivity is measured by standard scintillation procedures. The 50% inhibitory concentration ("$IC_{50}$") for mitogenic stimulation is determined graphically.

To evaluate differential effects on T- and B-lymphocytes, different mitogens are used: PWM (Sigma) at 20 μg/ml and Staphylococcus Protein A bound to Sepharose (SPA) (Sigma) 2 mg/ml or 14 μg/ml of Protein A.

LckBP1 and the fragments of the present invention show immunosuppressive activity when tested by this method.

Example 19

In Vivo Determination of Immunosuppressive Activity Utilizing the Hemolytic Plaque Forming Cell Assay This procedure is a modification of "The agar plaque technique for recognizing antibody producing cells," a procedure initially described by Jerne et al., [*Cellbound Antibodies*, Amos and Kaprowski editors (Wistar Institute Press, Philadelphia, 1963), p. 109].

Groups of 5–6 adult C578B1/6 male mice were sensitized with $1\times10^8$ sheep red blood cells ("SRBC") and simultaneously treated with an oral dosage form of the test material in an aqueous vehicle. Animals in a control group receive the same volume of vehicle. Four days after SRBC inoculation, spleens are dispersed in loose Ten Broeck homogenizers. The number of nucleated cells ("WBC") is determined and the spleen cell suspension is mixed with SRBC, guinea pig complement and agar solution at 0.5% concentration. Aliquots of the above mixture (0.1 ml) are dropped on four separate quadrants of a Petri dish and are covered with cover slips. After two hours incubation at 37° C., areas of hemolysis around plaque-forming cells ("PFC") are counted with a dissecting microscope. Total WBC/spleen, PFC/spleen and PFC/$10^6$ WBC ("PPM") are calculated for each mouse spleen. Geometric means of each treatment group are then compared with the vehicle-treated control group.

LckBP1 and the fragments of the present invention show immunosuppressive activity when tested by this method.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

---

What is claimed is:

1. An isolated LckBP1 protein of SEQ. ID NO:2 substantially free of proteins other than LckBP1 protein.

2. An isolated LckBP1 active fragment, said fragment having an amino acid sequence selected from the group consisting of SEQ. ID NOS:10, 11, and 13 to 29 substantially free of other proteins.

3. An isolated LckBP1 active fragment of claim 2 having an amino acid sequence selected from the group consisting of SEQ. ID NOS:10, 11 and 29.

4. A composition comprising a pharmaceutically acceptable excipient and the LckBP1 protein of claim 1.

5. A composition comprising a pharmaceutically acceptable excipient and an LckBP1 active fragment of claim 2.

* * * * *